(12) United States Patent
Kim et al.

(10) Patent No.: US 8,987,557 B2
(45) Date of Patent: Mar. 24, 2015

(54) PROMOTERS AND METHODS THEREOF

(75) Inventors: Ju-Kon Kim, Gyeonggi-do (KR);
Su-Hyun Park, Gyeonggi-do (KR);
Yang-Do Choi, Seoul (KR)

(73) Assignee: Myongji University Industry and Academia Cooperation Foundation, Gyeonggi-do (KR)

( * ) Notice: Subject to any disclaimer, the term of this patent is extended or adjusted under 35 U.S.C. 154(b) by 122 days.

(21) Appl. No.: 13/494,568

(22) Filed: Jun. 12, 2012

(65) Prior Publication Data

US 2013/0074219 A1  Mar. 21, 2013

Related U.S. Application Data

(63) Continuation-in-part of application No. 12/583,623, filed on Aug. 24, 2009, now Pat. No. 8,237,018.

(51) Int. Cl.
*A01H 1/00*  (2006.01)
*C12P 21/06*  (2006.01)
*C12N 15/82*  (2006.01)

(52) U.S. Cl.
CPC .................................. *C12N 15/8216* (2013.01)
USPC ........................................ 800/287; 435/69.1

(58) Field of Classification Search
None
See application file for complete search history.

(56) References Cited

U.S. PATENT DOCUMENTS

| 4,940,838 A | 7/1990 | Schilperoort et al. |
| 6,958,434 B2 | 10/2005 | Kim et al. |
| 7,365,185 B2 | 4/2008 | Boukharov et al. |

FOREIGN PATENT DOCUMENTS

| EP | 0116718 A1 | 8/1984 |
| EP | 0120516 A2 | 10/1984 |
| EP | 0301316 A2 | 2/1989 |

OTHER PUBLICATIONS

Sequence Accession AP003831, Sasaki et al, Feb. 16, 2008.*
In-Cheol Jang et al., "Subcellular targeting of green fluorescent protein to plastids in transgenic rice plants provides a high-level expression system", Molecular Breeding, 1999, pp. 453-461, vol. 5, Kluwer Academic Publishers, The Natherlands.
Sequence Accession ACL37128, Kreps et al., Jun. 2, 2005.

\* cited by examiner

*Primary Examiner* — Elizabeth McElwain
(74) *Attorney, Agent, or Firm* — IP Legal Services, LLC

(57) ABSTRACT

A promoter, which may be used to transform a plant and/or express a gene substantially uniformly in substantially all organs and/or tissues of a plant, and which may include a constitutive expression promoter for transforming a monocot plant. A vector including a promoter, which may include a recombinant plant expression vector. A method of producing a target protein using a vector, and a method of producing a transformed cell and/or plant using a vector. A transformed plant, a transformed seed and a transformed cell are included, which may be formed by the method of producing the same using a vector.

3 Claims, 8 Drawing Sheets
(4 of 8 Drawing Sheet(s) Filed in Color)

SEQUENCE LISTING

```
<160> NUMBER OF SEQ ID NOS: 110

<210> SEQ ID NO 1
<211> LENGTH: 1673
<212> TYPE: DNA
<213> ORGANISM: Oryza sativa
<220> FEATURE:
<221> NAME/KEY: promoter
<222> LOCATION: (1)..(1673)
<223> OTHER INFORMATION: Ascorbate peroxidase promoter

<400> SEQUENCE: 1
gtaaggtgac atggcatatc tatgtggtga ttttggtggg accaaggact atatcagccc      60
acatgacaaa tttaaaggac ttgtttggac aatatgaaag attaaggact aaaatgacct     120
aggagcgaaa ctttagggac catattggct attctccctt tttgacacga atgaaaaatc     180
caatttcata acttgtctgg aaaccgcgag acgaatcttt tgagcctaat taatccgtca     240
ttagcacatg cgaattactg tagcacttat ggttaattat ggactaatta agctcaaaag     300
attcgtcttg cgatttcctt tttaactgtg taattagttt ttcttttact ctatatttaa     360
tgctccatgc atatgtctaa agatttgatt taatgttttt cgaaaaaact tttggaggac     420
taaccgggcc taacgtgact tgaagagctg tgacagcgca aatcgtgaaa cgcggatgga     480
cctagcatta tggtgatgta ggaagtgcct tgctggcagt ggcaggtacc gtgcaagtgt     540
aataccatag atccgttggc ttatctgatt acatgatgat gattactccc tccgtttcac     600
aaatataagt cattttagca tttttcacat ttatattgat gttatgtcta gattcattaa     660
catcaatatg aatgtgggaa atgctagaat gacttacatt gtgaaacgga tcattaacat     720
caatatgaat gtggaaaatg ctagaatgac ttacactgtg aaacggaggg agtatacgat     780
tatgtaatga aaaaggagt acaatactag tcgccgtctc cccgcaaaaa aagtactagt     840
tgtcgtcaag tagggagta ataataataa taataataag ggataatata caggctgtgt     900
ttagatcgtg tgccaaattt ttttaaagta tacgacaaa tatttaaata ttaaacatag     960
actaataaca aaacaaatta cagattccat ctgtaaactg cgagacgaat ctattaaacc    1020
taattaattc gttattagca aatgtttact gtagcaccac attatcaaat catggcgtaa    1080
ttagctcaaa agattcgtct cgcgatttac atgcaaacca tgcaattgat ttttttttca    1140
tctacgttta gttctatgca tgtgtccaaa tattcgatgt gatgaaaaaa ttggtaattc    1200
gaggaaaaaa tttaaatcta aacacggcca cagtataaaa aaaaatagta gcgttgttgt    1260
ttatgaaaga ggatggtaaa gtaagacaag ataacgcaag ggcctaaaaa agtggagacg    1320
aagaagaaga cggaatatat tgcattggaa aagtgagcgc ttgacgaga gaaaaactcg     1380 gattcaagcg tccatatcag tggacaccac caatgggagg tggccacgtg ggcaggtccc    1440
```

```
gggtggaatc tggcgcgttc acacgggagg ttccgaaatt acggcaacgc cactggagtg    1500
cgaggcgcag gatgtgagat ccacggcggg ggctccgcta ctagaaactt cttctggtcg    1560
tgggtggtac gcaccctcgc gcctcgcctt tatattacta gtaagaagat ctcatccctc    1620
cttggtgagg tgaggtgagt tgagttgggg attgattgat tgattcggat tgg           1673
```

<210> SEQ ID NO 2
<211> LENGTH: 1853
<212> TYPE: DNA
<213> ORGANISM: Oryza sativa
<220> FEATURE:
<221> NAME/KEY: promoter
<222> LOCATION: (1)..(1853)
<223> OTHER INFORMATION: SCP1 AP2 domain containing putative gene promoter

<400> SEQUENCE: 2

```
ttgactttt  ctgcgaagaa tcctgtttac ggcgcataat aagatcgaag aatcacgcct     60
aactgcatgc agatacagtg ccgagaacag aatcagatct gcggattaac ggaagacttg    120
ttttagcttc cgtctttta tctggccata tgaaacagtc tctcctaaaa atagaatcac     180
tgtatagtaa acaaatcttg ggattgtcag caagtgccaa gtccacgtag aggaaaatct    240
tccaaaatat atcgtgggtc atcagatgag agattctcgc acaaaacatg cttacgtgtc    300
aaacgaggca cgctacgaaa aaagaggaag ctgaccaatc gacggcccct ccgtggccac    360
atgtttttgc ccgcttttcc aaaaaaaatt ccgttccgtt ttacggtgcc gtttaccttt    420
ggccctcaag ttagctggaa acacaaaatc cttccaattc tgtcgtgggg cctctcacga    480
taatttcagc attaagtact ttatttattc taaaaatatc tatcgccatt tccatgtgtc    540
agaaattagt tctgagttaa ggacgtcttg attgggagat tagccttggc cgcgtggaat    600
ctcaaccata gaatcccaat ccccttcttt tccgttgccc tatcactaga tctggtcact    660
atgcagaagt gtaaggggcc cacatgtcnt gnagacgatg atgtacaggc caggcgtgta    720
ggtgaancnt ttatcatttg ctagccgcct catctcgccc attcgcttcc ccgtcataaa    780 gccccccaa  aaccctcccc acctctgcca tttggtgctt atcccatga gtggtgggga     840 cacatcgccc gggccccaca tgtcagctaa aaccccgca  tgcttccgga cggtagcacc    900
ggtaccgaga tttttactcc gcgaggtgac cgctctgtca ctgcgcgtgg gcccggacgt    960
agtagtggcc cacccgtcac tgtgttcgta gcaggcgact gtgcagaaat ctggtgcgtg   1020
aagccgcaga atatcagccg gaggcagaga ggccactccc gcgtgacatg agggaccata   1080
tggtggggtg ggcccacgcg tcagtgtgat ggggtgggg ataggcgcgt gagggagagg    1140
aatgggtgga ggagtgggag gggattaaat atcggcggag gagacgagcc caacccctt    1200 tgctcctctc gccgtttgg tcggggttt agcgagcgcg tgggaggccg gaggcgacga    1260
cgacgaccgc gccgccgtcg gagaagaagg ccgcggaagc accagtacca gcacccgtat   1320
atgtcttcta gccccttctc cgatctggtg gtagtcgtgc tcctcgtctg cgccgtcgtc   1380
gccgcagccg tcctcctccc cctcgtctgc gccgccgat ctatgcacca gaggctccac    1440
ggctggaaca agcccacgtc gatgctcagg tgcgtccggg tgcccctccc ccaccgtgaa   1500 attttttcatc tttggcgagg tttacgccga tctggagtgg atttgaccgg gtttcgcggc   1560
cggttcgtcc agatctggag ggttcttggt gggtttttgt ggggtttttg attgatgggt   1620
ttgtttctcg tctgtgattt tgcagggacg ggttcggggt caagtattcc gggttcctcc   1680
acataaggcc gtgtggtttc tgtcgaggag attgacggat tcgatcgatt cgtgttcgtc   1740
```

```
tccgtcaaat ttttgcacaa gagaaaaaaa aagtttcccc cttttagagt ttttcccctt    1800
cagttttgtc agtttttgtg aggaatttta gagttctttt ccggcaagag tta           1853
```

<210> SEQ ID NO 3
<211> LENGTH: 1889
<212> TYPE: DNA
<213> ORGANISM: Oryza sativa
<220> FEATURE:
<221> NAME/KEY: promoter
<222> LOCATION: (1)..(1889)
<223> OTHER INFORMATION: PGD1 Cytosolic phosphogluconate dehydrogenase promoter

<400> SEQUENCE: 3

```
tagatatgcc gaacatgacc aatatagaaa aggtcatatt tgtgaataga gagaagtaat     60
aatatgaata gcaaatacgg agtacgtata tagcatcata taacacatgg aagtctcttt    120
cagttagtta atctatcaca tgcgggattt gcggttaaaa gctctgttcc ccaaaacgat    180
aaactaatct aaaatcctcg caaaaaaatt taaaaaatct gtaatcttaa attcgaggaa    240
actcatgtga agaatgaggt ggtggtgacg tcaccaacaa acagatgcga aatggagaag    300
atgccctggc ctgcaactgg gccgagccgc cgttggtccg gtccacgttc tgattgccag    360
tttgccacca actccaactc catatggcac gtggggccca ccacgcccgt ggagacccag    420
gcccacaagt caggcagcaa ttttgacccg cctaccgccg ctgcggcggc tatctctgcg    480
aggcggtccg gtcccacccg tcagagagac gtcctgatcg cggcaggtgt gaaaggcaag    540
ggggatattt ggtgggctat ttaagcaggc ggtgcggtag gtggtcgact cgctgcacgc    600 cttccgcga tttcgtcagt tacccagatc tcatcttacg caggtgagct ccgatctccc    660
ctctcccgcg ctgcgatttt gatttgatcc gtcgcgccgc atcgcgtcgt cgcttggtag    720
gatcatccat ccgtcccccg cgcagcgcga gctgtctagt ttctgctcga ttttttagtt    780
cctgtttatg ggggagggag ggagagaggg agggattggg tggaggcgaa ccaggaatcg    840
tcctggcggt gtgatgtctg gatgaattgg attggcagcg tcttttagtg gctgagagat    900
tgtttccttg ttactgttcc gtggggttta caactttaga atttgtttct tcgacagcat    960
gcagcaactt ggtagaattt agctgcatgt tctaggtggt ttgttgctgc tgatcctgct   1020
cgtttggatc aacgattttt gggggggctga gattaattgg ttggtacagt cttggttagt   1080
tacatccatg ggaacatgca gttggttatt ggtttgcaca tggagtacta ctgctaatgg   1140
ggtagatata gacagtgtgt gcgccaaagc ttgctaccac tagttctttt aagtatagtg   1200
cctcccaatt accaatatta cctatttca gtgtaaagtg ttaaatagaa agattgcttc    1260
tgattgctat ctcctttact gaattggtag ttaggtgcac atcttccatt gtaacgtatg   1320
tgttaccatg gctcatgtac tagttatgct agatatgttg tgctgctaaa catatatact   1380
agaaagaatg ctaccactcg ttccttctgt tgttaattgt ggaatgtttt gcaatctcta   1440
gtttgtagct cacaactgac catatgattc cccatccaag tgtcgacctc atgtgtgatt   1500
tcataaataa aaaagagcat attttcagga tcctgttatg atcctcattt catacattta   1560
tatacctttt ccataataca tgaatgatgc ctcactcaat gctataaatg ttacattat    1620 atattacctc ctcctacaag tatgaaatat gaattgccat aggccataca aaagagccca   1680
ctccctatat tggactcgat aaatattttt agtacatagc tcttaacttg catgtcatag    1740
tctgatgtac tgtccttttt gaattggaaa ctctgttact ttataaaaag gattgacatt    1800
tgtattccat tgttaaaaga aaagcaacat ctgcacaaac tagtttgttc tgcgcatgat    1860
```

```
gtattgatac atttggtgca tctatctgc                                      1889
```

<210> SEQ ID NO 4
<211> LENGTH: 1800
<212> TYPE: DNA
<213> ORGANISM: Oryza sativa
<220> FEATURE:
<221> NAME/KEY: promoter
<222> LOCATION: (1)..(1800)
<223> OTHER INFORMATION: R1G1 putative R1G1 domain containing protein
      promoter

<400> SEQUENCE: 4

```
atagctgttg tactgatgtc gtgcctaatg aggaaattgg agtaactgtc taactgattc      60
aacagaggaa attaaatcca ggtgagggat gatcagtgaa tccaaatatt gtactaatga     120
tcatgagtat tttatgtggg cattcttctt gacttgaagt tgtaaccgga cataactgct     180
gctaggaatg tatgacttga agctttaagc actactacat ctgatgatcc ttacatgttg     240
agcaagaggc tggaagaaaa aaaggatgag agccttttaa cccatgtaac tccaatgctg     300
tctgcaaacc tttcagctgg ttgtgagttg tggctgcaga tctgtggaag ccactgagag     360
agcactaggt aaggtttcta tgttatatct gtaattctgt atatgtttaa tgtgttgtgc     420
tcatttaaaa aaagaactgc atagattcac aaactgcctg gagcttttcct cttcactttg     480
ctaatagtat tgaccacgtt tgggcttgt tgtgtgtttg gaaggagtgg gtctataggc      540
cgtcagtgtt taggcctact aattaagcca gttcagttgg gccttggctg cttccatgga     600
ttaattatga gactaatcgc agatactcgt acaccaatgc gagaatttgt caaatcaatt     660
ggatcagtat atatcttgcc tgtatgattc acatccatac gtttctatcg agttggttgg     720
aagatttgtg ccgtcgatga cagtgcagaa gagaagcttc cttgcaacta gtgtcgtggc     780
agaagcagag gtagacacat gaaatcgtgt tctaatccgt cgcagctagc tagcatggca     840
gcgacgtgtt tgacgatgac accaccttgc atatccagat gcctctgttt gacctggatg     900
gaacaaacaa taacgtacgt ttttcgagca tctaaatggt ataaattttt agagaaattt     960
ttatgtgtaa tttctttctt ataatatagt tttaaaatct gtttcacaac taatcaattc    1020
agtcgtttgt atcctcgaat cattttcatg ttcaacattc catccattta ggcatttatg    1080
cacagaaacg tagaatacat agtttgtcca tgctttaaac gaaagtaaa aagaaagag      1140
aaagacacat attcctctta aaacaatatt cgtttgagat ggtggaggga acaaaggcca    1200
ttgatttgct gcagggtccc tccctaacaa gctgtgatga ttctgtatac gacgatcgtg    1260
caattaagct agtgctttga agagacaga cagacagaca acttttttcc tcctaatacg     1320
atcggaagaa aactgtcgag cttttatgta gcgtataaac cttgactgtt gcgaggaaaa    1380
aaaagctgta ggaaacaaag aaatcgagga aatgaatttg tcctggtttc gtatatatgt    1440
acatgtacta tatgccaaaa acgcccgtgc ttaacagcta agaaatcggc caaaattcag    1500
gcaaacaaga gacaaagtta gcaggcaacg cgtcactacc gcgtgatcat ttcgacgcga    1560
aggcaatttg gccggtgatc cagcgcgtct cgtgcagtga atgaagtagc ttaatttgct    1620
agtccccaca gtacgtggc actctgccat gtcttctctt agtataaata tatgaagcc     1680
aaagccaaag ccagtcagtt catcagttgc agttcagagt tgcccactgc tactttactt    1740
tgcagctatt ttgcttctgc ttcttcttgt tcttgttgct gttggtaata ctgcgagaga    1800
```

<210> SEQ ID NO 5
<211> LENGTH: 1837

```
<212> TYPE: DNA
<213> ORGANISM: Oryza sativa
<220> FEATURE:
<221> NAME/KEY: promoter
<222> LOCATION: (1)..(1837)
<223> OTHER INFORMATION: EIF5 translation initiation factor EIF-5A
      promoter

<400> SEQUENCE: 5
ttgttccacc tcatcattaa gaaagcattc aatctaccta ctgatcatct cgcttgcacg      60 tttcagggt agaggagcac cagatatttt tcgaaatgaa gcagcacttc taaggaggtg     120
tgcctcacct tttagcagga ggtccctacc ttcatgttgt acaactaatc gagctaaact    180
tattcgtagg tattctttc cacccatca ttttgttagc tgcgcaggat gtagctgaac      240
gttgttgtat tgttgtatgg ggaagcatta tactctataca aattagcagg tttacctatc   300
tcagcttgtg taggcatgtg attgttctca agcaagggca gggtagattt gtagcgactg    360
tgtgtaaact agtacatcat gtactgtatg ttcaaactgc tattaggaaa tgtaacacat    420
gttattggac atttggactt ggatctggtt atgcaaaatg gttgaagcaa atttgagttt    480
ttcttttctg ctagtaggga aacgagtagg aatatttact cgagaggaat cttttgcttc    540
tcaagcacat tctttctttt ggagttgatc cagacattga attgtgtctc ttttggtgtt    600
gctccagaca tattgaagtg tgtgtatctg tttgacctga tgcgtttgcg tctggaatct    660
ttgctgcact aggatgctgt gacttccagc tagtgctatg ttgctagtat ctggcttcc     720 cctttctgg gtttttcacc atttgatctt ttagaacatt tatttaacaa atagataaaa     780
aaaagactta ttctgattct ttttttggca ccaccgttat tggtctcgtg gttcaacatg    840
accgtgccaa tgacattggc gctgttctac attctccggt ggactaatgt gaagtgatgc    900
caatatcatt ggcgttgtta cgttggacca caacgtcaat aatgttaatg ttgtgaaaat    960
gatttattcc taaatatgtt ttttaattc tattttaaa atcaattttt taaaaggatt     1020
ataatgtgaa aaatctggct ccccattctt agggatgtaa atttcagac ggtaaccta     1080 ctgcttaaaa gtattatgga aaggctcacc gggggtatgt atggatcatg tcaaatgact    1140
cagtagagca caaaagtgct ttctggggttt atcttaacct ttgtaccgtc catttatcgg   1200
taggagaaca cgtgccattt tttgctggct tacagatata tcgtgacagg tgacaaacac    1260
gcaaaggtac atttcagccg accaaaaaaa atgttgtaca gtgaactgca atntgcaatt    1320
ttcatcgtgc actactcctg ctagtgcacc acgacgacac gcaatcccag gcgaagcggc    1380
ttctgcgcgc tgcgaaaagt cagcagcaaa accgccgcct gccgttgggt gggcccacg     1440 tctatgaaaa ggacgagccg cttttgtctc acgtgcggcc ggatccggct ggacccttc    1500 gatccgacgg ctacgctagg tacgcgcggg cgccacccgg ccgaccaaag taactatcac    1560
gacgggccga gccgaatggg ccggcggaaa agcccatccc acggcccgct ctccgcggat    1620
gcggcgcctc atacataaat gtctcgctga gctccgcccg tccggaaccc tagtcgccgg    1680
atcgcgtctc tcccatcctc tcgcgcatcc tcctccgact acctcggtga gccgccgccg    1740
cctcttccac tctcgtcttc ttgatctgat ctaggggggtc gcggcgttcc tgacctgtgc    1800
gcgcctggtg gtggttgttg ttgttggtgg caggttg                              1837

<210> SEQ ID NO 6
<211> LENGTH: 1813
<212> TYPE: DNA
<213> ORGANISM: Oryza sativa
<220> FEATURE:
<221> NAME/KEY: promoter
```

```
<222> LOCATION: (1)..(1813)
<223> OTHER INFORMATION: PF1 promoter

<400> SEQUENCE: 6
ctcggtgaag atagagaagg tttagaaaat acatggttga acccaacaat tgtaccaagt      60
tcctccaccc attcaacgaa ttggccttca tcttttggct actaaaatca gcccatgacc     120 ccccccccccc ccgcctcgat gaatattttt ttgccacttg ccttctctta tttgatgact    180
ctactgcgga caagattctt ctaacatatt attgccctg atatgatcac taatatgtgg      240
aggtcatcgt caatcgtcca catgactctt taagtaaatt aagtaaaagg atctcaatct     300
ctcaggtgtt gtctcttccc tttgattgct tgagtacctt ggtggctatt tgtgtctttt    360
gacttgaaga atgggtgcgt tcgtctcgtt tgccgtgagt ctacaaaact atgagcttcc    420
tctaattcaa acccgcgtgt ttctaatcct cttcgtctca tagcctacaa cgcaagagtc    480
ttgatggttt atttctttta ccacatcatg tgacgcttac gatgttagtt tattatagat    540
ataatgcaca atttgttact ctattagtta acatgcaaag ttttgtagca gtagcctcct    600
atcatatctt gaaagttttt ttttacattc atttattttg cacgagaaat cctaccgtat    660
ccttatgttt ttggtacact cttgtgtttc caaggagcgt tgactattcg gcttgaataa    720
aggtgtgttt ggttgggtgg atggagcatg gataggagat ggccacccga gttttttgtgg   780 tgtttggttg gagggcaagg tggatggggc agcctagaat agggaatatt ccctcaatat    840
gctggatgag tgcatccggc cgatttggct ggatgaatcc atccagtttt ggactgggtg    900
atatgtccta ttccgattgg ctgtggttgg tttgatttcc tgttaagcaa gctccaaatg    960
atttttttct cctaaactgt ttgtctaatt tatgatttga ttacaccatt atattcgtta   1020
taattaaatc tttaaaacaa gatttcggat gattatattt tgataaaaaa aatatatatg   1080
ataaatgagt cccactaact tttggctttt cgtatctatg ctatatccct ccaaccaaac   1140
aagaaattgg atcgccatat ccatacaaac caaacagaaa attggatcgc cgtatccaat   1200
aaaatatgga tgaccatatc ctatccatgc atgaccgtga atcaaacaca ttataatagg   1260
cctccactca cgaatctgat catgggcttg tgcctgccag cctatgcatc attacttaat   1320
gggcctggac cctaaaattg tccaagttca tcacgcaaac aagatgtggc ccgtatcgga   1380
gattccctca acgaaaaggg cccatctccc ccgggctgct cggacgatgg cccacatact   1440
cacggcccac cgtatcctat cgtgcccat ccaaacacgc gcaaacaccg cacgtgcctg    1500
acccaaactc cgcaaacggg ccggatccga accagacgag gcccacgatc cggcccaaga   1560
ggagaaaccc tagcgaggaa gggagtgcct cctacccgct ataaattccc agccacgccg   1620
cctcctccca aaccctagaa gcccccctgc ctcctgcgcc tccgccgccg ccgccttctt   1680
cgtctgctgg tacgccgccc ttcgccgccg ccgcctccgc atccaatctg cgttgttctt   1740
ccgccgattt cgattgcctc acccttcgtt ttgtttcttg attgatctcg cagagttcgt   1800
agatcagctc gag                                                      1813

<210> SEQ ID NO 7
<211> LENGTH: 1894
<212> TYPE: DNA
<213> ORGANISM: Oryza sativa
<220> FEATURE:
<221> NAME/KEY: promoter
<222> LOCATION: (1)..(1894)
<223> OTHER INFORMATION: PF2 promoter

<400> SEQUENCE: 7
```

| | |
|---|---|
| caacgggaca ctgtcgattc ccctcgcccg ctccctcccc attactccac ggcaacgggg | 60 |
| aggggatcca ccggcagcgc cgcttcccct cggccactcc ctcacccatc ctccaccagc | 120 |
| tccaccggcg gcgctctccc tctcggcaca gagtcggcgg ccctccgccc cttctcgcct | 180 |
| tcttcccgcg ccagatcagg cggggtggagg agtcggtggc ggtggcttcc tccgcccccct | 240 |
| ctcgccttcc ttccgccaca gatcgggcgg cggtggcggc cgcggctgga ttcggtggcg | 300 |
| gagaacggat tcggcggcag tggcggcggc tccttccacc ctcgcctccc tccctcggca | 360 |
| gaaacgacag cggtggcgag cggcggcggc gtagctcggc aagccacgac tggcggccac | 420 |
| tccatgcccc ctcctcgtca gatctggcca tgggagacgg tggcggctgc ggcaaactcc | 480 |
| gctcgatttt tggtcaattt gttttttta atctccgttt gctgttcttc tattcttgta | 540 |
| tttgggatca aacttgatta aaactttgtg tgttatttgc tgcggactct ggatgatttg | 600 |
| ttgtgtgttc ggacttatga tgttgtggac aaaaataggt gaagacggac gaaacacctc | 660 |
| acggaatcct tgtgttattt gatgcggacc ctggatgatt ttttatgaa cattatggac | 720 |
| tgttttaat cggacagatt cggttttttt tcgcccttttc ttttaccat gtcgcatata | 780 |
| atcggattcc atttttttgc ccgattcttt tgtcgcctat ttttcacgg acggatgacg | 840 |
| gaaacactcg taattttgta agtggtagag attttttcct tttttacata agacggaaac | 900 |
| tcttttttcg cactccttttt taatcgacca gaattttttt tgcactttttt ttggatcttg | 960 |
| gttttttttg gcacagacga cggattttttt taatcggaca gaataattt ttcgcgttat | 1020 |
| ttttttcctttt tttacggaag acagaaaccc ttttttgcc ttttttaat cggacagaaa | 1080 |
| tttttcgcac tttcttttgt cgcttgtttt ttcgtacaaa aatctttttt ttggcactct | 1140 |
| tttttgaagt cggaaaccgt ttttcgcacc tttttttttc tgggaatcgg acagaaaata | 1200 |
| tttttcgcac ttttttttgg aaattttttct taacttttta agtagcagag atagagatat | 1260 |
| atgcacgtgt tctcctggtg atgctaaccg aataggaccc ggattttcta gatcggacag | 1320 |
| ttttggtttt tcttttcttt ttccgcactt cttttttcgcc cggtttttta tcggacaaac | 1380 |
| ctgatttttt tcgttcggtt tttttgatga acgatggaag cacctctttt ttaagtagta | 1440 |
| gaggtagaga ttcatgatcc tttaacactg aatgatggcg aaagcggaca agtccaaacg | 1500 |
| attccgtgcc gccccccgctg acctcccttc ggccgccaca aacgcatctg agccgtccgc | 1560 |
| ctccgaatat ccgtccccaa tatcccgatc ggacggcagg caatcaacca cgtactcctc | 1620 |
| ccggcttctc ccccactcaa aagcccaaac cggcacaaat cggagatctg ggccgtccat | 1680 |
| cggtaatatt cccacggcat cagccagatc ggacggccag aatcgcggcc cagatatttc | 1740 |
| ggcccgctta taaataccgg ctggtcgcct ccacctcaaa ccctctctct ccgtccgtcc | 1800 |
| gcgccgctac tccccctcg ccgagagagc tctagggttt ccgctgccga atttttttttt | 1860 |
| taattcgggg ggagagattt gaagaggcgg cacc | 1894 |

<210> SEQ ID NO 8
<211> LENGTH: 1747
<212> TYPE: DNA
<213> ORGANISM: Oryza sativa
<220> FEATURE:
<221> NAME/KEY: promoter
<222> LOCATION: (1)..(1747)
<223> OTHER INFORMATION: PF3 promoter

<400> SEQUENCE: 8

| | |
|---|---|
| tcgttccaac gtaccgcaat accctctata tccagtctac gggtatcccc catcgacagg | 60 |
| atggattaca agttaataga cctaagtgat acctcgaatc aagtataatg actagccatg | 120 |

-continued

```
tattgtataa aaaaactttt aggtagatcg tttgagtcaa ctcatcccag agtatggcta      180
gatggatgaa aaagctcatg gatcgttagc tcatccaacg catggcttgg ctcgttgcac      240
tctcgtaata agttgagctc acattttagc tgctcatcag gctgctcaag agtcaaataa      300
gccaaggcaa gcagtggcca acacaacaac ccaacaagat aaaatcccaa ctccaccctt      360
aatccgtatg ccacctatga tggcattcca ttctatatcc aacttgactc ccatccgtcc      420
tctgttctta cgtcaccact tgtcgttcc gccacccatc aacatggtcg caacgctgcc       480
tcaacatatc atagctcaag caactccgtt catgctcttg cctatcgcct cactccatcc      540
ctatcttgct taccactcta cttcatcctc ggcagacaaa ccatgacata taacatgccg      600
atacttgact ccatctccgt cttatcgaac cgtcatggtt tcacgccaac gcgcgcaacc     660
gcattccctc gacgcaccac taggtcatgt agtaggaaga tgagatgcaa gacaaggcac      720
ctctgcccga caagtttgaa gtcaaagaac tcacataatg agaagagaca gtcgtcatca     780
tcataggtgg actttgagtt gatgtttatt ctcctagctc gctagcttaa tgagccaagc     840
ggagccagat cgagccaaat cgaactgatt cattattcag ccctattcct agagagacat     900
tcatggtaga ccttctaagt gtggtgccat ttgaatgtag acccaatcta tgtgtagagt      960
ggactaatgt gaatttgaat gttaacatgt tacgccagtc aatgtgatat catatcaatc     1020
agtagtacgg taataattca attatatgtt gtaatccctc cctgccaaaa taaattcatc    1080
tttatcccct cctatttgtc caaaaataag tttactttta agaaaaaat tatcaaagtt      1140 tgtgaaagta tgcgacaaat gtattggaag tagataaaaa tggaacaatt ctattaggat     1200
ttggttgggt ggagggtatt acagtctttt tgcttttgta tttatgggac aagagaaaat     1260
aaaattattt cgggacggat gtactaacat atacttcctc cgtccctaaa tatatgacgt    1320
tgttgacttt ttaaaacatt tttgaccatt cgtcttattt aaaaactttt gtgaaatatg     1380
aaaactatat atatacgaaa aatatatttt aataatgaat caaatgatag aaaaaaatta    1440
ttaattactt aatttttttg aataagacga acggtcaaac atgtttaaaa aaatcaatgg     1500
tgtcaaatat ttagggacgg aggaagtact tctctcgggt ccaaaattaa ttgcaaaccc    1560
gaatccatta tcccctacac caaaaataag ttttttcattt ttctcctttt agactgaccg    1620
aagctctgaa taaccgggca ggccacctat aagaatagca ttcacggggt ctgtgatccg     1680
tattcttagt gaccaccccc catatcacat cctctccttc ctcttcctct gctcactcag     1740
ctctccc                                                              1747
```

<210> SEQ ID NO 9
<211> LENGTH: 1774
<212> TYPE: DNA
<213> ORGANISM: Oryza sativa
<220> FEATURE:
<221> NAME/KEY: promoter
<222> LOCATION: (1)..(1774)
<223> OTHER INFORMATION: PF4 promoter

<400> SEQUENCE: 9

```
tctggcatcg atatgctcct tccattcatc ctgagagtga gacatgtttt tttctatgtt      60
atgtgcgtgg ttttattggg taaacattgt agaaagacag tcgggcgaca tcggcttata     120
ctaaggggag aatatatgct gggaagagaa cttgaagggg actaattctg attatttatt     180
gctaaattcc aaagactagc taaataccct atatatagag ccgacacctg caactcaatc    240
taatctaatc ctacttttaa gcaacagagt atatgtaaca cgcgctgcat tggaggcatg    300
```

```
gaggcattat atctaacacc caccttgttt ccctgcatgg aggcattccc tagtttacta      360
gcttgctcag tccgttttgc tcctttcaat ctcaaaatta tatagatcct tatgtttgat      420 gttattttg tcattaccgg tctcttcacg ttattccatt atgttaggtg ccaagaagag       480
tatgttggac cattagagtg gacatgatta gggatgcaag tggatagttc ctctactcgc      540 aaaaaaccc gtttgctagt tcatttctta catgatagta taaaatttag aagaaaaat       600 gaagtagaag tgagattagc gggctaaaga aacccgcttg catccctaga catgatccat      660
ccaccttctt attattaggt tgtaggctgc cattttttcta ccagccattt acaagattgc     720
caaccagatt cgctctgctc tcgtagccac tttacaccac tacgcagaac tacaaatcta     780
caggatggat ttgcattgcg agcatgatgt ccccaacttt aatacaaaac tgccaatata     840
taatgagttc agcaacgtgt tagggtaaag tttttttttt ttttttgcgc agaggcagtt     900
ggaaaaaaaa acctaagacc cctatcccat ataaaaaaaa ccaacttgta gcttacaaac     960
ctagataata agctagaagt ttattttta tgagtaaaac aggtggcttg acagtaattc     1020
tgatggcagt gttcttttga agggattgga gcatatccca ctcgcacgca aacaaagtga    1080
caaattaatg cacgattaat taagtattag cttaaaaagt ttgaaaaatg aattaatttg    1140
atttttacag taacttttgt gtaatttttt ttaaaaaaag tgcaccattt aaccgtttgg    1200
gatatgtgca tgtggaaaac aagaaatatg tggttgaaac cttgagggag aacacagcca   1260
aaacaaaaaa aaatctgatg gaatcaagaa ggccaacgtt ggtgtgggcc gggcccaatg   1320
catcatttcc ttcgtacgtt gcaatctagg cccaacggac tgcccaccac cccctcgcc   1380 tgaagaatgg ggtggatcag atggcaggct cattcccagc cgtcggatcg acccgatcac   1440
cgcctgcgaa gtaaacccta agccacggcc gcctccctat ataagcccac ccactagggt  1500
ttcgcccgcc tctcctcccc cccgctagtt cccaaccagc agctgcggcg gcgcgagcac  1560
acgaagagga ggcggagcag ccggagccac ctccgccgcc gccgccacca tgggtaaggc  1620
acgcccgcaa cccgggtgct caaccttcct cctccgctta cccccatccg cgtgggggt   1680 tgtggagttc gttgtttggg ttttttgcgt gtgtgtgtgc tgatggattg atgggggtgc   1740
ggtgatggct gtgcaggtat ctcgcgtgac tcca                               1774
```

```
<210> SEQ ID NO 10
<211> LENGTH: 1970
<212> TYPE: DNA
<213> ORGANISM: Oryza sativa
<220> FEATURE:
<221> NAME/KEY: promoter
<222> LOCATION: (1)..(1970)
<223> OTHER INFORMATION: PF5 promoter

<400> SEQUENCE: 10
gctgattccg tgcacctcat cgtcgctttc ctcctcttcc aaagaaagct gtgcgaattc       60
atcggggaaa ttcctgccca tgtacttggc tgtgccatcg ccatcagtca gctgctcatt      120
tgaactcgac ctccatggcc gctcattctt ggctgctgga aaaggaacaa caagcagttc      180
agttgcacat ctacattgaa caataactga aacgctcacc cgcgttcccc tctccgtacg      240
cacctcgccg gcagctcgag agcctccgcg gtgacggctc ataccggcaa cgacccatcg      300
ccttcgtcct gaagaagagg cattttgagg agagcgaatt aggacagctg agagatcgaa      360
aaggggatcg agggagcggg tggagactgg agaggtacca ggaagggtag gggattaggg      420
cacgggagcg caggcgcagc cctagctccg gccgcagatg gagcaggcgg cgactcgcgg      480
ccatggccgc cgccgccgcc atcctgagcg tctggtgcac tgacgccgcc gcggatggtt      540
```

```
tgaagcacag ttttactcca catcccgttt atctcaccat ctcgttaata acagagtaga    600
acaactatca tcagaacttc agagggacct gtttggatag ttgtcatttg ttaatggaaa    660
cctcattaaa caatagggaa ccgtaatttta tctattttt ttaaaaacac agtatataca    720
catacacaca tactcccttc gtctcataaa aaatcaacct aatactcctc catctcataa    780
aaaatcaaca tagtactaga tgtgacagat cccagtacaa cgaatctgga catccctaat    840
gtgtcacatt caatactaaa ttcactttct ttttagaaac ggagggatta cgtttatatg    900
tttatataac atgcacactc gccaaaccac atgcatccta ttattttgaa attcatgaag    960
tcaaactaca cgcgcgtttt gttatcgatt ggtacattgc ttatcattga aagaaaagta   1020
agttccacca ccataaatct aaccaatata aatactttca ctgtgtgtaa tttatctact   1080
tttattagat taagatatgc atctattcgc tttcaagatt tcctgcagtg gtcgaaaggg   1140
gaaaacaaat cgattccttg tggttttaaa ttataataat gcaggtcaac tgatatagtt   1200
gtatgtaaaa cgggttcata tgtatggatg ctacaagtta tacattatat tcaattctaa   1260
ctttcggaaa tattatatag tggtgtagat tgatttatgt agtacggatt aattggcatt   1320
gatgtataca aaatcagtt gtatatggaa aacctaatag ttgtatatta agaattactc    1380
caatccaatt taaatcgagc tctgtataga attgtaaggg aaaaaacgct aagttaaaaa   1440
tagatataaa ctctgtaaag atgcaggtgt ccaggctaaa cttccaagat catccaataa   1500
aaggaacact tcctttact tttctcctta ggaaaaaaa gaaaaaaaag aaagcgaaga     1560
gcaccgaaag gcgaatctaa gcgcgtccag cgtaagcatc acgcgagtcg tcggcgcgcg   1620
cggatccccg atcggacggt ccacgttgcc ccgtcgccct ataaattggt cccccgtct    1680 ccccacccca aatcctcccc gactcctcgc agcttcctct tgtttttctt ggccgaaccc   1740
cccctcgaca cgccgtcgcc gccgagggga gagagagaga ggccgccggc cgccgctacc   1800
actgaccccc cccctcgccg gagcgccccg tcgccggtcg gtacgcgtct ctaggccccc   1860
ctctctctct cgatttgatc ggtttgatct gtggtgccct aggtttgatc tgtggattta   1920 tttttttct tgttttgtgg gggtgattag ggtttgatcg atggcgtcca              1970
```

<210> SEQ ID NO 11
<211> LENGTH: 1753
<212> TYPE: DNA
<213> ORGANISM: Oryza sativa
<220> FEATURE:
<221> NAME/KEY: promoter
<222> LOCATION: (1)..(1753)
<223> OTHER INFORMATION: PF6 promoter

<400> SEQUENCE: 11

```
ggaccaaccg aagtccttcc ggaggaaaga ggggaaaaat ccgagcaagc gagcaagctc     60
aggttgccac cggtgacact tcacctgagc aagctcgctc ggtctctaca ggttgcttta    120
tctgaacgca aaagcgatat tccatggaaa agctctcagg cccacggcct cattagacaa    180
ggcccaacgc tcaagtttct tgaggcggc acatttagat aaggaaatgt ctgagggaat     240
aagatcacgg aggtccctca acctaacagc gagatgagat ttttgagatc ccttacccctt   300 aaactcacat aaaccatgca atcaaagtcc tatgatagta tatatgagcg gttttgctga    360
cgtggcatcc tagtcagtca aataaaaaac aaaaaagtta tggggcctaa agtaagtga     420 gaaggaaaaa atatgagacc cacatatctt ccttttctct ttcttctcct ctcttctctt    480
tgccactgag ggggagcggc agcaggcggt gacaaggaac cggagcaggc aggcgagtgc    540
```

```
tcggcggctg acggagtgga gcggggtggt ggcagcaggc gagcgcacgt ctggagcagc    600
gtggctgtga gcgcgcgacc gacacagtgg agcggcggtg gcaagcaagt gatgttgcga    660
gtgcgactag tggagcggag cgggcagtgg tggcgcgggt gctcggcgac gccgacgccg    720
tcgcgcttgg ccacgccac gccaccaacc acctccccct catctcctcc tcctcttctt    780
cctcttcccc aaactgcgac atctgccagg agacccacgc ctacttcttt tgcgtcgcgg    840
atcacgccct gctctgtcgg acctgcgaca cgtcgtcca catcgccaat gccttcatct    900
ccgcccattg caggttcctt ctcaccggcg tccacgtcgc ccttgacac caccctctg    960 ctccttcgca cctggagcca ctgttcgctc gccgcgtccc aagcccctct gcacctcctg    1020
agcccggagc cgccgctcgc ccgccgacgt cgccgctccg cctgcctccg gccgcacgcc    1080
gccgctgctc cccttctacg gcaaatataa aatgaagag aagaagagaa aaagtaaaag    1140
agcggcaaag ataaaaatga agagaagaag agaaaaagga aaagagaagg agattggtga    1200
ctagatcgtt gaccacatat ttttttttctc acttacatgt ggatcccaca tttttattta    1260 ttttattttta tgctgattag gatgtcatgt cagcaaaatc gggcaaaaat tgagtcgata    1320
ctgccatggg acctcctttg aacggtttga gtgagtttag gggtacaaat ttctggttct    1380
gtggttaagg gacctaaaaa attctcgctg ttaagttgag ggatctccgg tgaacttatt    1440
gcaatgtctg agagacaacg aagtgataga ttgggcctcc agcccacgag agtagaagtc    1500
ccagtcgcac gtttcgtcgc ctataaatac tctccccctt gggcagccac aaaccctagt    1560
cgaggagagc acccaacccc tgcgccgcca cctccgatcg tcagccatgg taaggagctc    1620
gccgcttccg gatccaccct agccgccgcg cggcggcgg ccgcttcggc gtcttcttct    1680
tctccgctca atctcccggt tagtcccttc tgattggttt cctccttcc ctcgcagacc    1740 ttcaagcgca gga    1753
```

<210> SEQ ID NO 12
<211> LENGTH: 1900
<212> TYPE: DNA
<213> ORGANISM: Oryza sativa
<220> FEATURE:
<221> NAME/KEY: promoter
<222> LOCATION: (1)..(1900)
<223> OTHER INFORMATION: PF7 promoter

<400> SEQUENCE: 12

```
aactgaacag ggccttacca gaaaatctct cgctggtccg ggtattgaac tgttttcgat    60
ggttccctcc ctctctttct ctacttggca tattaacgtt tttcattcct ttactttttc    120
attacgaaaa acgattttca ttcctttaac tagttattct tttaagtctc ttttaacgga    180
gaaaattgta atattgggac tgcaaacacg tgggcttcgt tgttttgaca ctccgagtgg    240
atgacaaatg ggtccatctg tatgtatgaa atataggcag tgtcattata gtaaaggtta    300
atgtttgcag tgttataatt gcaaatcccc cttttaacgt gttcttagaa ttaactagtt    360
gattggtaaa tagaaaatcc ctaaccaact taaaaaatta ttttttttaaa aaaaactgtt    420 tctaatcatt tttataacta atgagtaatt ataatttagt gctactcata aattttttact    480 tttacgagta caaattttac tcataaatta atttttattgc ttcatacatt tttgcgcgca    540
tatgtatttg aaatcactac cctctaattg gtaatagcac cccctccag tcacaccaga    600 atgagtatca atccaacgtc tacaaatgat aacacaaatt gatacactaa catatgacaa    660
attcatgggg aaggctaatg cgcacgtacg cgccagcaat ttagctggca cgcgcgggcc    720
ccctctcggt tcggtgcttt tattttttatt tttcttttct tttacgtttt tgcgctcaga    780
```

```
tctaggtgct tttttttttt attttttcgc catttctttc taatttttttt aatcttttcgc    840 acacctcttt ataaatgtag aattgaaagt ttttaatttt gacatgaaag ttttaaaatt    900
tcgacttgaa aattttaaat ttttgacttg aaagttttca aatttgcctt gaaagtttta    960
aaatttaagt tgaatgtttt caaattttgg gtgaaagttt ttaaatttga catgaaagtt   1020
ttcaaatctg agttgaaagt ttttaaatcg gggttgaaag ttttcaaatc tgggctgaaa   1080
gttttaaatt tgacttgaaa gttttttcaaa tttgagatga aaagttgaaa ttttttcaaaa  1140 tttgagatga aaagttgaaa gttttcaaaa tttgacttaa aaagattcaa gttgaaagtt   1200
ttcaaatttg aattgaaaat ttttaaattt aagttaaaag ttttaaaata tgggttgaaa   1260
gctttcagaa tttgactcag cgtataaatt tcttttcaat ttattactta aaaaaatctt   1320
cgggaaaaaa caaatcttat cttaattatc gtcattatct ataactaatg attctaaaac   1380
taatggatta gcgtggtgga aaaagaatc ccgaaaaaaa attttcgtcg acccgcaacc    1440
acgtatacac gtgagccgtg ggccggaagt gcgcaccgcc ggcgcgtatg cgcgaattag   1500
gaatctcgca aattcatgct tcattctgta ttgtttttt tttttttgaaa aaaggacccct  1560 tcagcccatg ctgcacgtag ctaaggccca aaccagccca caaagaaaaa gcagaatccc   1620
accactccgg cccacgaggc ccaccacctc aaaaccctag ccgctcccct cgcctcgtct   1680
cctctatata ggtatccctc ctcgcgccgc caccctcctt cccctttaagcc ggaggccgac  1740 acgaggtaag aagcccagaa gccctagcgc cgccgcagca gcagcagcca tggtgagctc   1800
gccgccgccc gccgaccctg ttcgttccgt aggatttgtc ttcccgctcg ctgacgctgc   1860
tgtttgtatg ttgctccgca gggtatcgac ctcgttgccg                         1900

<210> SEQ ID NO 13
<211> LENGTH: 1886
<212> TYPE: DNA
<213> ORGANISM: Oryza sativa
<220> FEATURE:
<221> NAME/KEY: promoter
<222> LOCATION: (1)..(1886)
<223> OTHER INFORMATION: SC1 promoter

<400> SEQUENCE: 13
gatcacttgt ggcagccata cttgaggcat ctcgatcgtt ttcaggacgt ctctggcttg     60
acagctgagt tgagattatt caggttgatc ttttttgcttg gttcagattt cagatccgtc   120
agacttttca attctgtttt cctactcgtt ttacaggttc tgaaattgcc aaatgccgac    180
caaacgaact caacacaaga cgtgattctg ttggtattgg gaggagatag gaaggaaaaaa  240 cctgtcctgc aaatgcaaaa atgcaatatg ccatattgcc ttccaatgag agtatgtcag   300
cattcaagca aacagccaaa cacagattat agttcgtccc atagaggctg gatgtggaac   360
gttagccaaa aactggattt gtaatcctaa ttttaattca ttttaggcgt tccttttcaa   420
attttttaag gctgtgttta gttccttcta aaattagaag tttgggttga aattggtacg   480
atgtaactga aaatttgcgt gtgtatgtca ggttgatgtg atggaaaaag ttggaagttt    540
ggatctaaac acagcctaag tttcggcttt ttaaccaaat atcaatatac taaacgccta   600
ccgtaaaact acttttcgt aacatcgttt ttattctatg gcttataact cgaagcctat    660
caatgtgact agtactattt tattacttaa tgaaacgtct atacattata tatcaaaaa    720 tgttataaaa ccgtaaaaaa gccatgatat caaactgaca aaataatact ctatccatcc   780
taaaatataa ggaattttat gtggatgtga cgtatcttat actttgggtg agaggaagag   840
```

```
gtactaatac cactattata ttgtactccc tccatactcg taaaagaaat cgtttaggac    900
agcgacacgg tttccaaaac acaactttga cttcttattt ctataaaagt atttattgaa    960
aagtgatata tgtatacttt tataaaatta tttttcaaga caaatctata tatataattt   1020
ttatattttc aaactcaaca acttaaaagt tatttatgat ttatattcct aagatttgat   1080
ttaagcattg tcctaaacta cttctttat aagtatggag taatatgtat tggtaacagt    1140
acagtatata cagcagtagt agtagaatat actgtactgt aggggaggt ttgggccggc    1200 agaggaatgg gccagtcgca catgccgtct gcgtgcgctt cccgcgacct agaatatcgc   1260
ccactcgctc aaccgcatat cccttcctaa taacctctcc gatccgtaaa cctcgcccat   1320
gcgccacgtc cccctagtg tcctacctcc cggaccaccc ggtcttggta gaccacgtcc    1380
acctccccaa ctaaaatatc ctccctaacc caaccacccc acgtaaccc acgtacttaa    1440 cgcgagttac ccccgcaaa gatccaaccg cctctcgcac cgcccgcctg tccacccacg    1500
cctactgacg aacccggccc acctctccgg gccccaccat gtcgtcacca cgcaggccaa   1560
aatcggggag agcgtgtcgt ggtcccacct gtcattggct tcgtgggtgg gagcgggtca   1620
cgtgcatctc gacatgactc gaggaggtaa ccatggttat ggtaacccca ccgccttgac   1680
acccgtggtt aggggtgggg gcgcgcgatg ccgccacgtg tgacgatcgg acggctgcgg   1740
agggcatcgg ggttgggcga cccgccatt taaccgcggg ggcctcgtct tcctcaggcc    1800
acgcagcgat ctgaagtgaa acagcaaaaa aaatcaaaca aaagaaaaa atattcccca   1860 tctgtgaaat tcgcaaaacc ctagcg                                       1886

<210> SEQ ID NO 14
<211> LENGTH: 1978
<212> TYPE: DNA
<213> ORGANISM: Oryza sativa
<220> FEATURE:
<221> NAME/KEY: promoter
<222> LOCATION: (1)..(1978)
<223> OTHER INFORMATION: SC2 promoter

<400> SEQUENCE: 14
ttacgtatag cctttcctt cggttttccc tggctgacga gtgacaaaac tgcagttgag      60
cacatgcggc aaaagaacac ccccagcgtc atcgtgccac gtggatggcc cccgcaccaa    120
atcaaacggc ccccgcgaga ggaacgccac aaccaacctc tcccctcct ctccgcagcc    180 gcacactccc gtcacgttgc ggtacggaca cccacacaca cagagacacg ctccgcctct    240
cactgatccg tgggaccacc gatccgcggc acgccagttc gggccaatca gagcccaggg    300
atccacgctg gcgatccgcg ggcagtcact caccccccgg ctcccacccc caccgccgtc    360
cgatcgtggc ggaggaaaca cacccgcgga cgatctcggc cgtccgacca cgcgggcgga    420
tataccaacc gggcgggggg tgggggattc ctcgctataa ataggaggcc gccgcttggc    480
tgagcaattt ttctgcggtt tcttcttctt cttcctcctc ctcgcgctcc cccgattcga    540
agcgtgaaga gaggaacggc gcttgcgaga ggagagaggt aagcatcacg gcgaagtttc    600
cccctctctc tttctttttcg tctcgtttgc tgcgaccccg gcggggtatt gagattctcc    660
gttgaggtcg gttggttggg ggcttggggg attgggtggg ttagggcttg ggggtggggg    720
gaatttggcg atttgggggg ttttctcggg tgatctgctt gttttttgcgc cgtttcgccc    780 ggtgaatgcc agcccgtgt gatttgctgg tttggttgtg gtctaatcgt ctgatattcc    840
agggctgtgt agtcctgtag ttttttgacta ggtaattgga gtgctgatgg gatttgccgt    900
tgaattttag gttgtttagc tctaatttac ctgcaacgtt ttgggaatta gggtttcttg    960
```

-continued

```
gtgaatttta ggttgtttag ctttaatttta cctgcaacgt tttgggaatt agggtttatt      1020
ggtgatatag tggatacgca tcgtaaactt gtatttagga ttccccttgg gattttgtag      1080
gcgagtggcg gctgtatgtg attggcacga attatttact cgggtgaatt tagactagct      1140
attttattgt tgccgtgccc tttctggata tgaacggatg aatatggcgt cactgctcga      1200
tgatatcgca atgttatgat tgaaaaagca tagtagttat actgatgcca ttgtgtagta      1260
gttagtttgt acctcccctg ggttgcattg caacttgcgt taatatggat actccgtaca      1320
attgtttatt gtttacttgg tatagctatg ctgcattttc tatatttgtt gggttataag      1380
tttttgtcca atattttttaa tgacttgtgc cagaggctct caatcctctg ttattagacc      1440
tgtaattgta aggtctattt ctccttcatt ctgtttcaat gttagtttgt ggatgtacag      1500
aaatcaagct atgattgata taatacattg ctttggcata atggcactct tattttttgtt     1560 ttatttagga gagtgctgtg tattagtttg ttcagttaat tcaatgttgt atgttttact      1620
gtgtcgggaa cttacagatg ttctctttag gtttctatcc attagtaagt agagttgttg      1680
ctttgcttga aaccatcaat ttgaatctgt ttatagagat aggctgttat tcctgcttac      1740
tattttttat atagttactt tgccatccgt taatcaggtt aagaacaata aattgtgtcc      1800
ataatcaatg ttttcaatgg aactcacaaa attttgacag aaacatgttg ctttcttagg      1860
tcaatctcta gcatattgtt tttttttttga attgttactt gtttctgtgg tgttattaca    1920
gaaagtgctt acttccactc tagaattttta ttacattttt gtcacagcat attctgtc      1978

<210> SEQ ID NO 15
<211> LENGTH: 1785
<212> TYPE: DNA
<213> ORGANISM: Oryza sativa
<220> FEATURE:
<221> NAME/KEY: promoter
<222> LOCATION: (1)..(1785)
<223> OTHER INFORMATION: SC3 promoter

<400> SEQUENCE: 15
accgatgtag atgaatactt cctcggttta ggaattggga ttttatttat aagttataca       60
aagtaaatat aaaatggacg gtgcatattg attgaggtag aatattagta ctactgtttc      120 ttcttttttgg aatatactgc aaaacaacac taatgtaatg ttcggacaaa acttaaacgt     180
cattatgaat attattagct cttaataatc ggcaatagcc aataggtcag agacaaacac      240
ccatcagagg atccggattc gatcaggtga gtgccggaca aacagtatgc ggcgccatcg      300
cccgtcgccg ccgccggcta cttttctgtta gagcacgggc ctgtttagtt caagaaaaaa    360
aaattatttt tgaatgtcac attggacgtt taactagata tcgaaataga ttttttggaca    420 cgaataaaaa aactaatttc ataactcgtc tggaaacagc gagacgaatc atttgagcct     480
aattaatccg tcgttagtat acgtaggtta atgtagcact tatggctaat catgaactaa     540
ttagactcaa aagattcgtc tcgtgatttc ctccctaact gtgcaattag ttttttgtttt   600 tatctatatt taatgtttca tgtatgtgtc caaagattcg atgtaatgtt tttaggaaaa      660
aaatctgtga actaaacagg gcccaagttt agccaactac taactccaaa tcacatatag      720
tcaacttaat agtaattca tacaatagtt acatactaca ctattaatac ctgatcccac     780
ctgtcataca tacactgtct cttgaagtcc atgctacagc tggctacaaa tctttagctc      840
gctgctcttc tctttcttat tttatttttct taaaatatgt taccaaacga cgacacgtag    900
ccagaaacac ctcgacacga acaccccccat gtcacaccac accacaacac gatcagttca    960
```

-continued

```
acttttttt tctctttttt caaaatttca catccttttc catcaattt tctttacccc    1020
gcattattgc agaagcaaga aggagcaaat atgccctttt ctatttcttt cacctccct    1080
gattctttct tgggcgacaa accacaacct gccacgtact ctactctacc cgccgcgcgt   1140
cactagctaa tgacacgtgg gcctcgccca tgcccgggcc cacacgtcag cgggacacct   1200
cacctgcctg ccctgcgct gcgccggctg cgccttctgg agaaaggta aagaaagaca    1260
ggtcacccac gcacctcgcg cttaatttat ttgtttccat ttttattttt aattttttt    1320
cctcacgctt tctcggttcc atttggcttt attaataatt aattagactt tttcctcttg   1380
gctttataaa agagagcgct taaaccctct ccacctctcc atatccggct tccagacgct   1440
tctctcctcc tctaatctca agtctctgtc tcgtcgtcct cgcatctcca ctcgccatgg   1500
gtaattatgc tcacctccga atcgaattaa ttccccgtt tgattactgc tggtgcttcg    1560
cgtcctgatc tgattgatgt ttttttttct gattttttg gtgaatttc tggtggtgtt     1620
tttgggacg caggcaagat taagatcgga atcaacggtg agtttgctat ctgaattact   1680
acgagtttgt gctgtgctgg gtgtggtttc gttggatttg tggtgatttg agtgggggtt   1740
ttttgtgtgt ttgggattgt gattttgttc aggtttcgga aggat                 1785
```

<210> SEQ ID NO 16
<211> LENGTH: 1886
<212> TYPE: DNA
<213> ORGANISM: Oryza sativa
<220> FEATURE:
<221> NAME/KEY: promoter
<222> LOCATION: (1)..(1886)
<223> OTHER INFORMATION: SC4 promoter

<400> SEQUENCE: 16

```
gctcgtagga caagcaggaa aagcagcgtt tgctcgtagt tgccatgaca aaatcgagat    60
aaaaaaaata acccaaaaga actgtaccta acattatact agcatgctgc atatatacaa   120
gagaagatat acataattac atatatcatt tgattaaccg ggaatggatc gaagacggcc   180
taccaaacgt gtacaagtgc attgcatctg gtcagtcagc cgcgtgcaga atgggcgaa    240
gaaactgtac aaagtgcatg gctagctaac atttactgtc acttcatcga tcgcactgag   300
tacgaaagac gagtagacga cgaccatcat tagtgacgtc cacgctaatt accctctcga   360
gtcaaacaca ggtgcaggac attagtgcgg ttaatatctt ggagtagtta attaaggcgt   420
taaatcatgt gcaaccgcac gatctctcgt tccgtccatt tgtggtgctg accacaggat   480
ggttgaagga caattgagca gtactgctca cttacatgtg agcccgagag gctatggggt   540
tcacatgtca gtgagcaata ttgcatgtac aatattgcag atgacctgca tggctgcatc   600
tggttgaagg gtagaaacac cacttttcca cttttttactc ccttgttttt catgcatatt   660
tcttcaacaa ctaaacattg tgtttttctt aaaaaaattt actatagaaa agttgaattt   720
ttaaaatcat attaatctat ttttattctt ttactaatat ttaatcatgt gctaatgaac   780
tatattgttt tctgtacaga aagaagaaga gccccatcgg ttgccttaat aagccaaagc   840
aaaagataaa atttgaattt ttaaacttaa ttttgaagtt gatttaaaga tttttttcaa   900
catagttttt ttttcagcat cgacttttaa atcgttaaga acacatgtat aaaaagtttt   960
accaataaat tagtttttta ttatctaatg aaccaaaatg gcttattaga aaatatgagt   1020
aaccgatgag gccggaagta tccaactaat actcttgaac acatagggcc tgttcatttt   1080
gatgccattt tcaaccatac cattttttttt gtcaaagttg ccaaaaaata tatacgtttta   1140
gtttgttacc aaatttggtc aatacataag aaatcctgcc aaaatgttgg caatattgcc   1200
```

```
atcttgttaa aatttggta ttgccaaaac ttggtaaggt ttattttggc tacaatctga    1260
acatgcctat aatagtagaa ggggtttatt tgcaaatatc catctccaac ttcacgtggg    1320
actatctgag tggattaaag tggtttagaa tctaataatc gaaacccatt ttgaaaaggg    1380
ttaaattatc aaatctctcc tcttgaccct ccctttcttt ccatgggctt cgccggcgac    1440
tggaccctct actgtcttga atgcgcttca tagcttgttt tcatagactt cattggcgac    1500
ttgatcctag tttgttttca tgggctttac gggccactgg accctcgctt gtcttcatgg    1560
gctttatggg cctcattttc ttcagaattt tatggccttc tatacgccca ctacacctaa    1620
tcacgcgcaa aatctcactg ccggtccggc ctggcccacc cgcaacgact agtcaacacg    1680
cgctgcggcc tcgccggctt ctaggcccac gtagaaggtt cgagaacaac gaggaccgca    1740
taaaagcatc tcccaccccc acgatctcgc cctctcaaaa ccctctccta acctagccg     1800 ccgccgcagc cgcagccgca gccgcgcgtc gtctcctccg cccgcgagct cctcttcccg    1860
ccggcgagag atcaggagca cgcaag                                          1886

<210> SEQ ID NO 17
<211> LENGTH: 1906
<212> TYPE: DNA
<213> ORGANISM: Oryza sativa
<220> FEATURE:
<221> NAME/KEY: promoter
<222> LOCATION: (1)..(1906)
<223> OTHER INFORMATION: SC5 promoter

<400> SEQUENCE: 17
tgtgacgtgg cagtctgaca cgtggggtac atgctgactc agctgccacg taggataaaa      60
acgggctcaa aaccaccgaa tgagttattg taaccggttt tggtaagtta aggaaccttg     120
atatctggtt ttgcggttcg aggacgtttt ttatctcggt agcaagttga gggaccttcg     180
gtgtactttt ccgaacgtga aatgggtggt atcatgatgg gctgttcaat ctgtcgatat     240
ttatgggctg aattaggctt acaggcttag ggcaagccga atttcgtggg ctattatggc     300
agcttttctc gtgcacaaat atggatcttt atttggccca ccgcgacccc acggcataac     360
gaaacaggca gagcccctgg aaagatttca gcaatacctg ttcagacgac gacgtctgct     420
ctgttgttcg atttccgtcc gcatattcgt cgtgtgatcg tgtccacgcc tggagttttc     480
tggcacaggc cgcgctcttc tcacctcagc ctcaggactc aggtgatcgt gtcaacgtcc     540
ggagctctca ggcgatcgtg tctcacttca caggttgaca ggtcggcgca ttcgatgccg     600
ttccaaacgc agaaaattta gagaaacatc tcggacagac gcggcgctcc cacgcgtgga     660
atcccgcaga tgtaaaactt cgttacaatt tacagtgttc gcaacatcaa gaaacgacat     720 ttttcattc gaaaatgctg caaatctgca actggcaatc tctagacaaa tccttttccct    780 ttcgatgccg aagcagaatt gaagtttgag aatgttcttc gtctagaccg agcagtcagt    840
gatctgcaag cgcgaggcgt tcacagatcg tctcgacgac ctccctcccc tgggacgcgt    900
tctgcctgaa cctctccgcg caccgccgct ccaccatctc ggccgcccag gccgccacgg    960
cagcgagcgg cgcgcaccga atgctcgtct cctgccggaa cagcgtccac tcgtcgggcc    1020
gctccgggtg cgggcggtag ctgcaggtct cctcgacgtg caccagcgcc ggaggttgg    1080 cgttgcggga gatcacccgc atggcccgtg cgggcccgtc cacggtggtg tgctcgacgc    1140
agagcaccac gtcggcggcg gcgacgaggc gcggaggag gagcgggagc ggcggcgccc    1200
gccccgcgat ggcgcgcacg gcgtcgatgc gccccgatcc agcgtcgacg cggcgggaca    1260
```

| | |
|---|---|
| gcgtgtgcac ctcgaggatg tgcgacagcg gcgccgcccg cgcgtccgcg tccgtgaact | 1320 |
| tgcgccacgc cgccgcggtc acccggtgcc acgggtggcg gtacacgtgc tcctgcgtgt | 1380 |
| acgagaccac catgccggcc ggccggccgc cgcttgcctg tgcgcgcgcg cgtcgcgtcg | 1440 |
| cgccgagatc gagcgaggct agcgagagcg atttcgacag caactgcagc gaaataatgg | 1500 |
| gaatatgagt gtgtgtggac tccggactcc ggaggaagag aggaatattc gagttccacg | 1560 |
| gggaattaaa cccattattt tgggctcaat ttgcttggac tgcaaagcta ccagacctgc | 1620 |
| agcccagcgc atctacagat gggccaaatt ttgacatact tcttagtggg cctaagaatt | 1680 |
| catgaattgg ggccggccta aggccagcag cccagtgagt catcacctcg cgacctaatg | 1740 |
| tctcgatcca acggcgaaga tcaaaaccct aacctgcgcc atcgtcgact atattaaaag | 1800 |
| cccactcctc cccgcgccgc cgcccttctc tcgagcaagc acccaaaccc tcccctctac | 1860 |
| cccgccgccg ccgccgagga aggggcaaga ggaagccggc gaagat | 1906 |

<210> SEQ ID NO 18
<211> LENGTH: 1842
<212> TYPE: DNA
<213> ORGANISM: Oryza sativa
<220> FEATURE:
<221> NAME/KEY: promoter
<222> LOCATION: (1)..(1842)
<223> OTHER INFORMATION: SC6 promoter

<400> SEQUENCE: 18

| | |
|---|---|
| gtgcactcaa ggtcctatgg tagtatatat gggtgatttc gctgacgtgg catcctagtc | 60 |
| agcaaaaaaa aattaaaaag tatatggggc ccacatgtca gctgcacatt ttattttctt | 120 |
| ctccttctcc tctctcttct catcttcagt gaaggaggcc agcggtgggc ggagcggcgg | 180 |
| cggtcgagca cagcgacggg tagagcagcg gtgggcaagc gcgtcagcgg agcggcgggg | 240 |
| ggctacgggc gtgcacgacg gctagtagag cagcgggggg cgagcgcggc ggcggtgaac | 300 |
| tacatctcca agaggggggg tggaggaggc caccggtgcc gtgtggtgca cggtcacccc | 360 |
| gaccgcaacc cgtccttgtc atggtcctcc ccttcatcga caagcctcct gaagtcgagg | 420 |
| tccatctcga ggagctcccc cgtgctcagc caccaccacc gcccgtgccc ccgcgagtgg | 480 |
| ctcatgatgc taggagcggc accaccagcg ggagaagggg aagaggcaga ggaggagatg | 540 |
| atttcttggt cactgattgc ctccctcgca tgcaagctag gcgagctcgg acgggctcgc | 600 |
| cggccgcctc cccttccctc ccaatctgct tcgcccgcgg cctgcatcca cgctcgccca | 660 |
| tcgccggcct ccctcattga agatgagaag agataagaga gagaaagag aaggagaaga | 720 |
| atagagaatg tgcagctgac atgtgggccc catgtacttt tttatttttt ttgctgacta | 780 |
| tgatgccacg tcagcgaaac cacccatata tatactgtca taggaccttg agtgcgcggt | 840 |
| ttgtgtgagt ttatgggtac acatttatgg ttttgtggtt aagggacctc aaaaaatctc | 900 |
| gttgttaagt tgagggacct ccggtgaact tattcatcaa aaaagatca ctaggtccaa | 960 |
| caaatctgac agacagacct tgcaaaggcc cattaaagca caattaactg ggcctgaaaa | 1020 |
| gcccagcccg tccactctga cgattctacc cctctaaccc tacaccggcc agcgactata | 1080 |
| taaaagcgga cccgtctcga gccgctaggg ttcttcgatt tctccctcgc gccgccgcct | 1140 |
| cctcctcacc ctccccgccc caggcgcacc ctacgcttgg agctcgtccg atccgctcgg | 1200 |
| cgcccgccat ggtaaacgcg cgaagctctg aatccatcct ctgttcctcg cggtctcgcg | 1260 |
| tgcgtgccgt gctgcttgct ggttgatgct aatctcctca ctcgcgtttc gcctgtttgt | 1320 |
| tgttgcagat catcccgaag aagaaccgca atgagatctg caagtacctc ttccaaggtc | 1380 |

```
agtggttctt ggtccctatt tgcacctcgt aatcgtacta gaggcgtaga gccgccgcca    1440
tgtttagtgg agattgttgt tttaggtttg caaaacgagg agattcgtgt tgctccgtac    1500
aggagcacgg ttcttagtgc aggaactgcc ctcttgttaa aaggagaagc ttggtttaga    1560
tgtaggattt gatatgctag tgataatttt tcattctagg aacccaatga actattggtt    1620
atatactagc gaaatctgtg cacccatgaa catcaactta aattgattgt ttcggtcctg    1680
gtgttgtgaa atctgtgtg taaaaatttc aagaaaaatg atatcgctgt tggtgtatgt    1740
cagtacagcg ttcgcatgcc aagaggctca aactgaaagt gattgtaggt gctggtttta    1800
acttggtgta tgctgttgtt gcagagggag tgctgtatgc ca                      1842
```

<210> SEQ ID NO 19
<211> LENGTH: 1876
<212> TYPE: DNA
<213> ORGANISM: Oryza sativa
<220> FEATURE:
<221> NAME/KEY: promoter
<222> LOCATION: (1)..(1876)
<223> OTHER INFORMATION: SC7 promoter

<400> SEQUENCE: 19

```
gtcgaactca ccgtgcacta tatcaaccgc cgaagaaata aattcttcgt caccatccga      60
tgaaaactca tccaatagca tttggaggag ggtgcttcga cgactcatct cctcttttttg    120 tttgccacgg tgttggagcg tttaccacag ggatgaagtg caatggaggg aactgatggc    180
aggaatagaa caataatcaa tctgcaaaat taattatcag atcaaactta atattttcca    240
acaatatata tccacatcaa aatactgaca tagagattga ctacggcaca agagattaat    300
gggatttgct aaggattacc tccttgatga cacgaattgc tacgacatct ccttggtgtt    360
ccgtttttta acaaatcgca gcagtcagga cactggttgg ctggctggtg atgatggcgc    420
taggtcacgg cggcgcaagt gtggggagga agaagtcgat cggcgctggt gcgggaggga    480
gaagacgtgc gcaagtaccg aactgggccc caccttgctt atgtggcaaa ctaacaaatg    540 ataggaatt gattttttggg cttctcttgg aggagggggt cattgttggg cccaatttt    600 attttggtat tcctaattca gatttttttgg gaatcaaata ttgggtgatt gttgggcatg    660
ctctaagtga tttgtttggt tgggagacat ggaaaattta gtgggataggg gatggtgaat    720 tgaggaagga actccctcct tttcaatacc tgggtagggg caggtaattg ggagggaatt    780
cctcctttac tttttctaag caaatctgag ccatctgttt ttattaatga cttaatctcc    840
aactaaactc cctatcaatt tccattacct ctaccaaaca agatattgag attaaaaatc    900
aaattcccat cttaatctca ttatcaattc cctcgtgtaa actcccaatc tccttccctc    960
gagttaccaa acaagccgtt agatcactaa gaatacgtat ataaaagttt tattcacaaa    1020
ttttttccat ttacaaatat gccgatgggt cctggtgatt tacttaacaa atgtttgatt    1080
agatcttcag ttttatatac aaattcgttt tgtctaaaca gataaaattg acttattaat    1140
cttgggaagg ccgttactca ctctagactt tactcctcct tatctttttt tttcttgaac    1200
gaacatttca tttcttatat ttttgcatag tttttttaag gtagttatag acaaaagtga    1260
taatgattgg gcttctaaat aatgggtaag acttgtctcc aacaagtgac ccataagggc    1320
acctaaatct aaaatggggtt tccgatagta ttatttcagc ctccaacaga gtacctatac    1380
agaagaccta ttttacgtgc tataagaggc ataacctaaa tctgagtatc ctctctcctg    1440
aagacctatt tgcagtaagg gttctctttt aggccttatt gttggagaag accaaaaata    1500
```

```
ggtattgaac tcttttactg tagcgctatg caaacgtgaa atgagtcttg tattttgggt    1560
ttcattgttg gagatagcct aaccaccacg cgccggaagc caaacccagt tctccccgtt    1620
cccgcctaca ttttcgccac gtcagcgatc cgcaccgaaa tgcatcgcag ccgtttacgg    1680
aaacagcatc gaacgtcaca cgttcgtcca cgttatcgat ccgtggggaa accactccac    1740
caatcagcgc ccacctcaag ttcgctataa agtcgtcgcc cccgtcccca ttctcttccc    1800
cacatcgcag tcttgcaaac acacgcagca aaatccacac cgcttcccct ccccgagaag    1860
aagagagcag catcca                                                    1876

<210> SEQ ID NO 20
<211> LENGTH: 1930
<212> TYPE: DNA
<213> ORGANISM: Oryza sativa
<220> FEATURE:
<221> NAME/KEY: promoter
<222> LOCATION: (1)..(1930)
<223> OTHER INFORMATION: SC8 promoter

<400> SEQUENCE: 20
aaaaaacttg actgcccaaa atctgctcca caggcattgg ccttgcaatt ggatatgttg      60
cgtttgtggt tgtgcctttg aagatacaaa tcatttgttc agtgattgtg tgtttgtcag     120
acaagtgtag accctaattt gtcaattcca aaacttgact tcggtcggaa taaatcctgt     180
cctggatgtg tcaacatggt ggtctggaac caaatttgca ggctctaaga aggatgtgca     240
gttggtcagg gaaactcttc taactacttg ctggaatatt tggttagaaa gaaatagaag     300
aattttccaa aactcttcct gttcagagat tgaagtagct tattttatca agcaagctat     360
tgatatgcgc tgcttggcct ttaaacccca ataatttttt ttagcttttc ctgtagctgt     420 attttatcttt ccattccttg gcttgtaacc tctgaacctc tgtgctactt tgtaatttct    480
ctctcctaat gttaaatttt ggcagatctc ctaccgtcgt tctcctcaaa aaataatat      540 aattatacca tggaaagaaa aaaaactgaa ggacacgtta gagatcgact caaatatcag     600
gggagtgcaa gggatttttct cttgttatta gaataatttt agtggcgcat ggcataaacg    660
aatgtgaagg caattatctt ggttgcagca tcgagctaag agatcaacac gagcagctga    720
agcgacaacg actacatggt cgcgaactca agagcagcag tgagggaagc caaggcattg    780
gcacttggca gaacaaagct gggtcgagga ggatattgat atcggggttg agtagattaa    840
attagacttg aaaaataggg aattgccaat gagttgatat atttgtcaac aaacatagtt    900
taatatattg taggccaaag acaagctatg tcaaaatcaa ctttctgcta atgtttaact    960 gagttttttaa tttcattttg aaaagtgatt cacatttgat gatgtctcaa gtgcctttag   1020
catcaagctt tccattctat ttcatttgta ctccacctgt tccaagattc tatttgtcac    1080
aaaatattca tatttaaact ttgaccattt gttttttctt taaaattaaa tacttataat    1140
atatcatatt attagggcgt gttgaagcct aacctaagca ttaatatttg ttcatcatag    1200
tctaatcact taaaaatagc catgatcgaa gttaaaacaa cgcttgtcaa acaaataaaa    1260
aagtatttgg aagcggatat agttattgcc tagcccggtc tagaacctca cagaaaatca    1320
cacctagtat atcttggaaa gccaaataaa gtggctaaat gaattaatcg attttttcacc   1380 caagaatttt atcagaacct tattgacttg aatttacaa caataaagag ttcagcatga    1440
cgcctttgca taatagcata atagtaccac ataaaaacca tggtagaatc tattatagaa    1500
ttgcgcattt atcgtgaaac attttgaaat caatatttgg tcaaaatttc ttatgtatac    1560
attaaaactt aaaaaaatcc agtactctaa aaaaaattgt aattctcgat acacaaaaat   1620
```

```
cgtcgcgtcc ctatgaccca tgggcccttc cacaatttcg ctcacgcgcg agaaaatccc    1680
gccccgcgct cgtctcttcg cgcccagata tttcaccacg tcagcaatcc gcgccgaaac    1740
gcatcccacc cgttcaccgc aaacagcggc gaacgacacg aatccttcca cgtcatcgat    1800
ccgcgccgca tgctttccac caatcagggc gcacatcccc tcttctataa aaccaatcgg    1860
ccccgtctcc tcctcttccc aaccgcaaat cttgcgatcc acacacagca aaagaaccac    1920 caccgttttcc                                                           1930

<210> SEQ ID NO 21
<211> LENGTH: 20
<212> TYPE: DNA
<213> ORGANISM: Artificial Sequence
<220> FEATURE:
<223> OTHER INFORMATION: APX forward primer

<400> SEQUENCE: 21
gacctctaga ccgccgtatt                                                   20

<210> SEQ ID NO 22
<211> LENGTH: 20
<212> TYPE: DNA
<213> ORGANISM: Artificial Sequence
<220> FEATURE:
<223> OTHER INFORMATION: APX reverse primer

<400> SEQUENCE: 22
gccaaccact cgcaatccaa                                                   20

<210> SEQ ID NO 23
<211> LENGTH: 20
<212> TYPE: DNA
<213> ORGANISM: Artificial Sequence
<220> FEATURE:
<223> OTHER INFORMATION: SCP1 forward primer

<400> SEQUENCE: 23
tcgctgccta cgccaacatc                                                   20

<210> SEQ ID NO 24
<211> LENGTH: 20
<212> TYPE: DNA
<213> ORGANISM: Artificial Sequence
<220> FEATURE:
<223> OTHER INFORMATION: SCP1 reverse primer

<400> SEQUENCE: 24
tcgccgaact agcaggtgag                                                   20

<210> SEQ ID NO 25
<211> LENGTH: 20
<212> TYPE: DNA
<213> ORGANISM: Artificial Sequence
<220> FEATURE:
<223> OTHER INFORMATION: PGD1 forward primer

<400> SEQUENCE: 25
ccgtgagcta gcgaggatct                                                   20

<210> SEQ ID NO 26
<211> LENGTH: 20
<212> TYPE: DNA
<213> ORGANISM: Artificial Sequence
<220> FEATURE:
```

<223> OTHER INFORMATION: PGD1 reverse primer

<400> SEQUENCE: 26
ccggtaggag tcgaagtacg                                          20

<210> SEQ ID NO 27
<211> LENGTH: 20
<212> TYPE: DNA
<213> ORGANISM: Artificial Sequence
<220> FEATURE:
<223> OTHER INFORMATION: R1G1 forward primer

<400> SEQUENCE: 27
cttctcgatt gccgtgtgct                                          20

<210> SEQ ID NO 28
<211> LENGTH: 20
<212> TYPE: DNA
<213> ORGANISM: Artificial Sequence
<220> FEATURE:
<223> OTHER INFORMATION: R1G1 reverse primer

<400> SEQUENCE: 28
gcaagtctca agctctcaat                                          20

<210> SEQ ID NO 29
<211> LENGTH: 20
<212> TYPE: DNA
<213> ORGANISM: Artificial Sequence
<220> FEATURE:
<223> OTHER INFORMATION: EIF5  forward primer

<400> SEQUENCE: 29
gatctgcgct ctgaaggata                                          20

<210> SEQ ID NO 30
<211> LENGTH: 20
<212> TYPE: DNA
<213> ORGANISM: Artificial Sequence
<220> FEATURE:
<223> OTHER INFORMATION: EIF5 reverse primer

<400> SEQUENCE: 30
aaccgcaaga tggaacaacg                                          20

<210> SEQ ID NO 31
<211> LENGTH: 20
<212> TYPE: DNA
<213> ORGANISM: Artificial Sequence
<220> FEATURE:
<223> OTHER INFORMATION: PF1 forward primer

<400> SEQUENCE: 31
ggtctcttcg ccaagctcct                                          20

<210> SEQ ID NO 32
<211> LENGTH: 20
<212> TYPE: DNA
<213> ORGANISM: Artificial Sequence
<220> FEATURE:
<223> OTHER INFORMATION: PF1 reverse primer

<400> SEQUENCE: 32
cgcctcctcc ttcttctcct                                          20

<210> SEQ ID NO 33
<211> LENGTH: 20
<212> TYPE: DNA
<213> ORGANISM: Artificial Sequence
<220> FEATURE:
<223> OTHER INFORMATION: PF2 forward primer

<400> SEQUENCE: 33
agctcaagga ccttcagttc                                               20

<210> SEQ ID NO 34
<211> LENGTH: 20
<212> TYPE: DNA
<213> ORGANISM: Artificial Sequence
<220> FEATURE:
<223> OTHER INFORMATION: PF2 reverse primer

<400> SEQUENCE: 34
acggcggact gcatagataa                                               20

<210> SEQ ID NO 35
<211> LENGTH: 20
<212> TYPE: DNA
<213> ORGANISM: Artificial Sequence
<220> FEATURE:
<223> OTHER INFORMATION: PF3 forward primer

<400> SEQUENCE: 35
ggtcactcca tcgtcagaat                                               20

<210> SEQ ID NO 36
<211> LENGTH: 20
<212> TYPE: DNA
<213> ORGANISM: Artificial Sequence
<220> FEATURE:
<223> OTHER INFORMATION: PF3 reverse primer

<400> SEQUENCE: 36
acttgctcca cactgatcac                                               20

<210> SEQ ID NO 37
<211> LENGTH: 20
<212> TYPE: DNA
<213> ORGANISM: Artificial Sequence
<220> FEATURE:
<223> OTHER INFORMATION: PF4 forward primer

<400> SEQUENCE: 37
caatgtggca gagctgatgg                                               20

<210> SEQ ID NO 38
<211> LENGTH: 20
<212> TYPE: DNA
<213> ORGANISM: Artificial Sequence
<220> FEATURE:
<223> OTHER INFORMATION: PF4 reverse primer

<400> SEQUENCE: 38
ggtctgtagg cacgacatag                                               20

<210> SEQ ID NO 39
<211> LENGTH: 20
<212> TYPE: DNA
<213> ORGANISM: Artificial Sequence
<220> FEATURE:
<223> OTHER INFORMATION: PF5 forward primer

```
<400> SEQUENCE: 39
ggagtcctgc acttaccata                                          20

<210> SEQ ID NO 40
<211> LENGTH: 20
<212> TYPE: DNA
<213> ORGANISM: Artificial Sequence
<220> FEATURE:
<223> OTHER INFORMATION: PF5 reverse primer

<400> SEQUENCE: 40
ccatggcgta cttctgtgtc                                          20

<210> SEQ ID NO 41
<211> LENGTH: 18
<212> TYPE: DNA
<213> ORGANISM: Artificial Sequence
<220> FEATURE:
<223> OTHER INFORMATION: PF6 forward primer

<400> SEQUENCE: 41
gaagctgtac gccaaggt                                            18

<210> SEQ ID NO 42
<211> LENGTH: 20
<212> TYPE: DNA
<213> ORGANISM: Artificial Sequence
<220> FEATURE:
<223> OTHER INFORMATION: PF6 reverse primer

<400> SEQUENCE: 42
taggtgcgag caacattagg                                          20

<210> SEQ ID NO 43
<211> LENGTH: 20
<212> TYPE: DNA
<213> ORGANISM: Artificial Sequence
<220> FEATURE:
<223> OTHER INFORMATION: PF7 forward primer

<400> SEQUENCE: 43
cacagccaca cgaagccata                                          20

<210> SEQ ID NO 44
<211> LENGTH: 20
<212> TYPE: DNA
<213> ORGANISM: Artificial Sequence
<220> FEATURE:
<223> OTHER INFORMATION: PF7 reverse primer

<400> SEQUENCE: 44
gcacaatgcc gatcgcaaca                                          20

<210> SEQ ID NO 45
<211> LENGTH: 20
<212> TYPE: DNA
<213> ORGANISM: Artificial Sequence
<220> FEATURE:
<223> OTHER INFORMATION: SC1 forward primer

<400> SEQUENCE: 45
agcaccttcc accgcgtgat                                          20

<210> SEQ ID NO 46
<211> LENGTH: 20
```

```
<212> TYPE: DNA
<213> ORGANISM: Artificial Sequence
<220> FEATURE:
<223> OTHER INFORMATION: SC1 reverse primer

<400> SEQUENCE: 46
ttcgccatgg acaggatgcc                                              20

<210> SEQ ID NO 47
<211> LENGTH: 20
<212> TYPE: DNA
<213> ORGANISM: Artificial Sequence
<220> FEATURE:
<223> OTHER INFORMATION: SC2 forward primer

<400> SEQUENCE: 47
ctgcggaggc ataccttgtt                                              20

<210> SEQ ID NO 48
<211> LENGTH: 20
<212> TYPE: DNA
<213> ORGANISM: Artificial Sequence
<220> FEATURE:
<223> OTHER INFORMATION: SC2 reverse primer

<400> SEQUENCE: 48
acactacgac gcatgcttca                                              20

<210> SEQ ID NO 49
<211> LENGTH: 20
<212> TYPE: DNA
<213> ORGANISM: Artificial Sequence
<220> FEATURE:
<223> OTHER INFORMATION: SC3 forward primer

<400> SEQUENCE: 49
aacgtggacg gtgttcatca                                              20

<210> SEQ ID NO 50
<211> LENGTH: 20
<212> TYPE: DNA
<213> ORGANISM: Artificial Sequence
<220> FEATURE:
<223> OTHER INFORMATION: SC3 reverse primer

<400> SEQUENCE: 50
caactgcact ggacggctta                                              20

<210> SEQ ID NO 51
<211> LENGTH: 20
<212> TYPE: DNA
<213> ORGANISM: Artificial Sequence
<220> FEATURE:
<223> OTHER INFORMATION: SC4 forward primer

<400> SEQUENCE: 51
aacaccttcg gcaccaggat                                              20

<210> SEQ ID NO 52
<211> LENGTH: 20
<212> TYPE: DNA
<213> ORGANISM: Artificial Sequence
<220> FEATURE:
<223> OTHER INFORMATION: SC4 reverse primer

<400> SEQUENCE: 52
```
aagcgaacag cagcagtcag                                                    20

<210> SEQ ID NO 53
<211> LENGTH: 18
<212> TYPE: DNA
<213> ORGANISM: Artificial Sequence
<220> FEATURE:
<223> OTHER INFORMATION: SC5 forward primer

<400> SEQUENCE: 53
catcttgcgg tcggagaa                                                      18

<210> SEQ ID NO 54
<211> LENGTH: 20
<212> TYPE: DNA
<213> ORGANISM: Artificial Sequence
<220> FEATURE:
<223> OTHER INFORMATION: SC5 reverse primer

<400> SEQUENCE: 54
tacgcatcct ctgtgatggt                                                    20

<210> SEQ ID NO 55
<211> LENGTH: 20
<212> TYPE: DNA
<213> ORGANISM: Artificial Sequence
<220> FEATURE:
<223> OTHER INFORMATION: SC6 forward primer

<400> SEQUENCE: 55
catttggttc tggcccacct                                                    20

<210> SEQ ID NO 56
<211> LENGTH: 20
<212> TYPE: DNA
<213> ORGANISM: Artificial Sequence
<220> FEATURE:
<223> OTHER INFORMATION: SC6 reverse primer

<400> SEQUENCE: 56
gtctgccacc agagctccta                                                    20

<210> SEQ ID NO 57
<211> LENGTH: 18
<212> TYPE: DNA
<213> ORGANISM: Artificial Sequence
<220> FEATURE:
<223> OTHER INFORMATION: SC7 forward primer

<400> SEQUENCE: 57
cgtcaccaag ttcacttc                                                      18

<210> SEQ ID NO 58
<211> LENGTH: 22
<212> TYPE: DNA
<213> ORGANISM: Artificial Sequence
<220> FEATURE:
<223> OTHER INFORMATION: SC7 reverse primer

<400> SEQUENCE: 58
ccacctaatt cttcttacag tc                                                 22

<210> SEQ ID NO 59
<211> LENGTH: 18
<212> TYPE: DNA
<213> ORGANISM: Artificial Sequence

```
<220> FEATURE:
<223> OTHER INFORMATION: SC8 forward primer

<400> SEQUENCE: 59
caaggctgtg accaagtt                                                 18

<210> SEQ ID NO 60
<211> LENGTH: 20
<212> TYPE: DNA
<213> ORGANISM: Artificial Sequence
<220> FEATURE:
<223> OTHER INFORMATION: SC8 reverse primer

<400> SEQUENCE: 60
ctacagcaca gtaccatacc                                               20

<210> SEQ ID NO 61
<211> LENGTH: 20
<212> TYPE: DNA
<213> ORGANISM: Artificial Sequence
<220> FEATURE:
<223> OTHER INFORMATION: OsCc1 forward primer

<400> SEQUENCE: 61
actctacggc caacaagaac                                               20

<210> SEQ ID NO 62
<211> LENGTH: 20
<212> TYPE: DNA
<213> ORGANISM: Artificial Sequence
<220> FEATURE:
<223> OTHER INFORMATION: OsCc1 reverse primer

<400> SEQUENCE: 62
ctcctgtggc ttcttcaacc                                               20

<210> SEQ ID NO 63
<211> LENGTH: 20
<212> TYPE: DNA
<213> ORGANISM: Artificial Sequence
<220> FEATURE:
<223> OTHER INFORMATION: Act1 forward primer

<400> SEQUENCE: 63
atggtgtcag ccacactgtc                                               20

<210> SEQ ID NO 64
<211> LENGTH: 20
<212> TYPE: DNA
<213> ORGANISM: Artificial Sequence
<220> FEATURE:
<223> OTHER INFORMATION: Act1 reverse primer

<400> SEQUENCE: 64
taaccacgct ccgtcaggat                                               20

<210> SEQ ID NO 65
<211> LENGTH: 20
<212> TYPE: DNA
<213> ORGANISM: Artificial Sequence
<220> FEATURE:
<223> OTHER INFORMATION: OsUbi forward primer

<400> SEQUENCE: 65
atggagctgc tgctgttcta                                               20
```

```
<210> SEQ ID NO 66
<211> LENGTH: 20
<212> TYPE: DNA
<213> ORGANISM: Artificial Sequence
<220> FEATURE:
<223> OTHER INFORMATION: OsUbi reverse primer

<400> SEQUENCE: 66
ttcttccatg ctgctctacc                                                  20

<210> SEQ ID NO 67
<211> LENGTH: 32
<212> TYPE: DNA
<213> ORGANISM: Artificial Sequence
<220> FEATURE:
<223> OTHER INFORMATION: APX promoter forward primer

<400> SEQUENCE: 67
aaaaagcagg ctgtaaggtg acatggcata tc                                    32

<210> SEQ ID NO 68
<211> LENGTH: 32
<212> TYPE: DNA
<213> ORGANISM: Artificial Sequence
<220> FEATURE:
<223> OTHER INFORMATION: APX promoter reverse primer

<400> SEQUENCE: 68
agaaagctgg gtccaatccg aatcaatcaa tc                                    32

<210> SEQ ID NO 69
<211> LENGTH: 32
<212> TYPE: DNA
<213> ORGANISM: Artificial Sequence
<220> FEATURE:
<223> OTHER INFORMATION: SCP1 promoter forward primer

<400> SEQUENCE: 69
aaaaagcagg ctttgacttt ttctgcgaag aa                                    32

<210> SEQ ID NO 70
<211> LENGTH: 32
<212> TYPE: DNA
<213> ORGANISM: Artificial Sequence
<220> FEATURE:
<223> OTHER INFORMATION: SCP1 promoter reverse primer

<400> SEQUENCE: 70
agaaagctgg gttaactctt gccggaaaag aa                                    32

<210> SEQ ID NO 71
<211> LENGTH: 32
<212> TYPE: DNA
<213> ORGANISM: Artificial Sequence
<220> FEATURE:
<223> OTHER INFORMATION: PGD1 promote forward primer

<400> SEQUENCE: 71
aaaaagcagg cttagatatg ccgaacatga cc                                    32

<210> SEQ ID NO 72
<211> LENGTH: 32
<212> TYPE: DNA
<213> ORGANISM: Artificial Sequence
<220> FEATURE:
<223> OTHER INFORMATION: PGD1 promote reverse primer
```

```
<400> SEQUENCE: 72
agaaagctgg gtgcagatag atgcaccaaa tg                                    32

<210> SEQ ID NO 73
<211> LENGTH: 32
<212> TYPE: DNA
<213> ORGANISM: Artificial Sequence
<220> FEATURE:
<223> OTHER INFORMATION: R1G1 promoter forward primer

<400> SEQUENCE: 73
aaaaagcagg ctatagctgt tgtactgatg tc                                    32

<210> SEQ ID NO 74
<211> LENGTH: 32
<212> TYPE: DNA
<213> ORGANISM: Artificial Sequence
<220> FEATURE:
<223> OTHER INFORMATION: R1G1  promoter reverse primer

<400> SEQUENCE: 74
agaaagctgg gttctctcgc agtattacca ac                                    32

<210> SEQ ID NO 75
<211> LENGTH: 32
<212> TYPE: DNA
<213> ORGANISM: Artificial Sequence
<220> FEATURE:
<223> OTHER INFORMATION: EIF-5A promoter forward primer

<400> SEQUENCE: 75
aaaaagcagg ctttgttcca cctcatcatt aa                                    32

<210> SEQ ID NO 76
<211> LENGTH: 32
<212> TYPE: DNA
<213> ORGANISM: Artificial Sequence
<220> FEATURE:
<223> OTHER INFORMATION: EIF-5A reverse primer

<400> SEQUENCE: 76
agaaagctgg gtcaacctgc caccaacaac aa                                    32

<210> SEQ ID NO 77
<211> LENGTH: 32
<212> TYPE: DNA
<213> ORGANISM: Artificial Sequence
<220> FEATURE:
<223> OTHER INFORMATION: PF1 promoter forward primer

<400> SEQUENCE: 77
aaaaagcagg ctctcggtga agatagagaa gg                                    32

<210> SEQ ID NO 78
<211> LENGTH: 32
<212> TYPE: DNA
<213> ORGANISM: Artificial Sequence
<220> FEATURE:
<223> OTHER INFORMATION: PF1 promoter reverse primer

<400> SEQUENCE: 78
agaaagctgg gtctcgagct gatctacgaa ct                                    32

<210> SEQ ID NO 79
```

```
<211> LENGTH: 32
<212> TYPE: DNA
<213> ORGANISM: Artificial Sequence
<220> FEATURE:
<223> OTHER INFORMATION: PF2 promoter forward primer

<400> SEQUENCE: 79
aaaaagcagg ctcaacggga cactgtcgat tc                                32

<210> SEQ ID NO 80
<211> LENGTH: 32
<212> TYPE: DNA
<213> ORGANISM: Artificial Sequence
<220> FEATURE:
<223> OTHER INFORMATION: PF2 promoter reverse primer

<400> SEQUENCE: 80
agaaagctgg gtggtgccgc ctcttcaaat ct                                32

<210> SEQ ID NO 81
<211> LENGTH: 32
<212> TYPE: DNA
<213> ORGANISM: Artificial Sequence
<220> FEATURE:
<223> OTHER INFORMATION: PF3 promoter forward primer

<400> SEQUENCE: 81
aaaaagcagg cttcgttcca acgtaccgca at                                32

<210> SEQ ID NO 82
<211> LENGTH: 32
<212> TYPE: DNA
<213> ORGANISM: Artificial Sequence
<220> FEATURE:
<223> OTHER INFORMATION: PF3 promoter reverse primer

<400> SEQUENCE: 82
agaaagctgg gtgggagagc tgagtgagca ga                                32

<210> SEQ ID NO 83
<211> LENGTH: 32
<212> TYPE: DNA
<213> ORGANISM: Artificial Sequence
<220> FEATURE:
<223> OTHER INFORMATION: PF4 promoter forward primer

<400> SEQUENCE: 83
aaaaagcagg cttctggcat cgatatgctc ct                                32

<210> SEQ ID NO 84
<211> LENGTH: 32
<212> TYPE: DNA
<213> ORGANISM: Artificial Sequence
<220> FEATURE:
<223> OTHER INFORMATION: PF4 promoter reverse primer

<400> SEQUENCE: 84
agaaagctgg gttggagtca cgcgagatac ct                                32

<210> SEQ ID NO 85
<211> LENGTH: 32
<212> TYPE: DNA
<213> ORGANISM: Artificial Sequence
<220> FEATURE:
<223> OTHER INFORMATION: PF5 promoter forward primer

<400> SEQUENCE: 85
```
aaaaagcagg ctgctgattc cgtgcacctc at                                     32

<210> SEQ ID NO 86
<211> LENGTH: 32
<212> TYPE: DNA
<213> ORGANISM: Artificial Sequence
<220> FEATURE:
<223> OTHER INFORMATION: PF5 promoter reverse primer

<400> SEQUENCE: 86
agaaagctgg gtgatcctct tggacgccat cg                                     32

<210> SEQ ID NO 87
<211> LENGTH: 32
<212> TYPE: DNA
<213> ORGANISM: Artificial Sequence
<220> FEATURE:
<223> OTHER INFORMATION: PF6 promoter forward primer

<400> SEQUENCE: 87
aaaaagcagg ctggaccaac cgaagtcctt cc                                     32

<210> SEQ ID NO 88
<211> LENGTH: 30
<212> TYPE: DNA
<213> ORGANISM: Artificial Sequence
<220> FEATURE:
<223> OTHER INFORMATION: PF6 promoter reverse primer

<400> SEQUENCE: 88
agaaagctgg gttcctgcgc ttgaaggtct                                        30

<210> SEQ ID NO 89
<211> LENGTH: 32
<212> TYPE: DNA
<213> ORGANISM: Artificial Sequence
<220> FEATURE:
<223> OTHER INFORMATION: PF7 promoter forward primer

<400> SEQUENCE: 89
aaaaagcagg ctaactgaac agggccttac ca                                     32

<210> SEQ ID NO 90
<211> LENGTH: 30
<212> TYPE: DNA
<213> ORGANISM: Artificial Sequence
<220> FEATURE:
<223> OTHER INFORMATION: PF7 promoter reverse primer

<400> SEQUENCE: 90
agaaagctgg gtcggcaacg aggtcgatac                                        30

<210> SEQ ID NO 91
<211> LENGTH: 32
<212> TYPE: DNA
<213> ORGANISM: Artificial Sequence
<220> FEATURE:
<223> OTHER INFORMATION: SC1 promoter forward primer

<400> SEQUENCE: 91
aaaaagcagg ctgatcactt gtggcagcca ta                                     32

<210> SEQ ID NO 92
<211> LENGTH: 32
<212> TYPE: DNA

```
<213> ORGANISM: Artificial Sequence
<220> FEATURE:
<223> OTHER INFORMATION: SC1 promoter reverse primer

<400> SEQUENCE: 92
agaaagctgg gtcgctaggg ttttgcgaat tt                             32

<210> SEQ ID NO 93
<211> LENGTH: 32
<212> TYPE: DNA
<213> ORGANISM: Artificial Sequence
<220> FEATURE:
<223> OTHER INFORMATION: SC2 promoter forward primer

<400> SEQUENCE: 93
aaaaagcagg ctttacgtat agccttttcc tt                             32

<210> SEQ ID NO 94
<211> LENGTH: 32
<212> TYPE: DNA
<213> ORGANISM: Artificial Sequence
<220> FEATURE:
<223> OTHER INFORMATION: SC2 promoter reverse primer

<400> SEQUENCE: 94
agaaagctgg gtgacagaat atgctgtgac aa                             32

<210> SEQ ID NO 95
<211> LENGTH: 34
<212> TYPE: DNA
<213> ORGANISM: Artificial Sequence
<220> FEATURE:
<223> OTHER INFORMATION: SC3 promoter forward primer

<400> SEQUENCE: 95
aaaaagcagg ctaccgatgt agatgaatac ttcc                           34

<210> SEQ ID NO 96
<211> LENGTH: 31
<212> TYPE: DNA
<213> ORGANISM: Artificial Sequence
<220> FEATURE:
<223> OTHER INFORMATION: SC3 promoter reverse primer

<400> SEQUENCE: 96
agaaagctgg gtatccttcc gaaacctgaa c                              31

<210> SEQ ID NO 97
<211> LENGTH: 32
<212> TYPE: DNA
<213> ORGANISM: Artificial Sequence
<220> FEATURE:
<223> OTHER INFORMATION: SC4 promoter forward primer

<400> SEQUENCE: 97
aaaaagcagg ctgctcgtag gacaagcagg aa                             32

<210> SEQ ID NO 98
<211> LENGTH: 32
<212> TYPE: DNA
<213> ORGANISM: Artificial Sequence
<220> FEATURE:
<223> OTHER INFORMATION: SC4 promoter reverse primer

<400> SEQUENCE: 98
agaaagctgg gtcttgcgtg ctcctgatct ct                             32
```

<210> SEQ ID NO 99
<211> LENGTH: 32
<212> TYPE: DNA
<213> ORGANISM: Artificial Sequence
<220> FEATURE:
<223> OTHER INFORMATION: SC5 promoter forward primer

<400> SEQUENCE: 99
aaaaagcagg cttcctcttg ccccttcctc gg                                32

<210> SEQ ID NO 100
<211> LENGTH: 32
<212> TYPE: DNA
<213> ORGANISM: Artificial Sequence
<220> FEATURE:
<223> OTHER INFORMATION: SC5 promoter reverse primer

<400> SEQUENCE: 100
agaaagctgg gttgtgacgt ggcagtctga ca                                32

<210> SEQ ID NO 101
<211> LENGTH: 32
<212> TYPE: DNA
<213> ORGANISM: Artificial Sequence
<220> FEATURE:
<223> OTHER INFORMATION: SC6 promoter forward primer

<400> SEQUENCE: 101
aaaaagcagg ctgtgcactc aaggtcctat gg                                32

<210> SEQ ID NO 102
<211> LENGTH: 32
<212> TYPE: DNA
<213> ORGANISM: Artificial Sequence
<220> FEATURE:
<223> OTHER INFORMATION: SC6 promoter reverse primer

<400> SEQUENCE: 102
agaaagctgg gttggcatac agcactccct ct                                32

<210> SEQ ID NO 103
<211> LENGTH: 32
<212> TYPE: DNA
<213> ORGANISM: Artificial Sequence
<220> FEATURE:
<223> OTHER INFORMATION: SC7 promoter forward primer

<400> SEQUENCE: 103
aaaaagcagg ctgtcgaact caccgtgcac ta                                32

<210> SEQ ID NO 104
<211> LENGTH: 34
<212> TYPE: DNA
<213> ORGANISM: Artificial Sequence
<220> FEATURE:
<223> OTHER INFORMATION: SC7 promoter reverse primer

<400> SEQUENCE: 104
agaaagctgg gttggatgct gctctcttct tctc                              34

<210> SEQ ID NO 105
<211> LENGTH: 33
<212> TYPE: DNA
<213> ORGANISM: Artificial Sequence
<220> FEATURE:

```
<223> OTHER INFORMATION: SC8 promoter forward primer

<400> SEQUENCE: 105
aaaaagcagg ctaaaaaact tgactgccca aaa                                    33

<210> SEQ ID NO 106
<211> LENGTH: 30
<212> TYPE: DNA
<213> ORGANISM: Artificial Sequence
<220> FEATURE:
<223> OTHER INFORMATION: SC8 promoter reverse primer

<400> SEQUENCE: 106
agaaagctgg gtggaaacgg tggtggttct                                        30

<210> SEQ ID NO 107
<211> LENGTH: 29
<212> TYPE: DNA
<213> ORGANISM: Artificial Sequence
<220> FEATURE:
<223> OTHER INFORMATION: attB1 adaptor primer

<400> SEQUENCE: 107
ggggacaagt ttgtacaaaa aagcaggct                                         29

<210> SEQ ID NO 108
<211> LENGTH: 29
<212> TYPE: DNA
<213> ORGANISM: Artificial Sequence
<220> FEATURE:
<223> OTHER INFORMATION: attB2 adaptor primer

<400> SEQUENCE: 108
ggggaccact ttgtacaaga aagctgggt                                         29

<210> SEQ ID NO 109
<211> LENGTH: 21
<212> TYPE: DNA
<213> ORGANISM: Artificial Sequence
<220> FEATURE:
<223> OTHER INFORMATION: GFP forward primer

<400> SEQUENCE: 109
cagcacgact tcttcaagtc c                                                 21

<210> SEQ ID NO 110
<211> LENGTH: 21
<212> TYPE: DNA
<213> ORGANISM: Artificial Sequence
<220> FEATURE:
<223> OTHER INFORMATION: GFP reverse primer

<400> SEQUENCE: 110
cttcagctcg atgcggttca c                                                 21
```

PROMOTERS AND METHODS THEREOF

CROSS REFERENCE TO RELATED APPLICATIONS

This application claims the benefit of a prior-filed U.S. patent application Ser. No. 12/583,623 (filed on Aug. 24, 2009), now issued as U.S. Pat. No. 8,237,018 under 35 U.S.C. §120, which is hereby incorporated by reference in its entirety.

BACKGROUND

The present invention generally relates to promoters and methods of use and fabrication thereof, and particularly to a promoter used to express a gene, a vector including a promoter, a method of producing a target protein, a method of producing a transformed cell and/or a plant, a transformed plant, a transformed seed, a transformed cell, and PCR primers for a promoter.

A promoter may relate to a genomic region located upstream of a structural gene and may function in the transcription of a structural gene, for example, into mRNA. A promoter may be activated by binding of general transcription factors, and may include base sequences such as a TATA box and/or CAT box which may assist to regulate gene expression. For example, promoters linked to genes may be constitutively activated by general transcription factors to express genes associated with proteins needed tier the basal metabolism of a living organism and which may be required in cells at a given concentration. Promoters may also be activated when proteins are needed which are not ordinarily present or only required under special circumstances. For example, inducible promoters may be activated by binding of specific transcription factors, which may be activated in an organism's developmental processes or by external stimuli resulting from surrounding environmental factors.

A foreign gene (i.e., transgene) introduced into a plant, forming a plant having novel characteristics which may develop an agricultural field, may be influenced by transcriptional, post-transcriptional translational and post-translational elements. A promoter may belong to a transcriptional element and may directly influence transcription of a transgene, for example, to change the expression level of a transgene. A promoter may be the most important factor to change the expression stage or the tissue and/or cell specificity of a transgene.

Although promoters have been isolated from plants to express a transgene, only a few promoters may be practical for use in the transformation of plants. For example, a CaMV (cauliflower mosaic virus) 35S promoter and its derivatives may induce expression of genes in plant tissues and exhibit high activity, for example in vascular tissues and root/leave cells. However, a CAW 35S promoter has relatively less activity in monocot plants, such as a rice plant, and does not exhibit any activity in certain cells, such as pollen.

Promoters from dicot plants which have been investigated for the transformation of monocot plants have exhibited relatively lower activity compared to promoters originating from monocot plants. A rbcS (ribulose bisphosphate carboxylase/oxygenase small subunit) promoter of rice, a Act1 (actin1) promoter of rice, and a Ubi1 promoter of maize are examples of promoters from monocot plants which have been investigated in the transformation of monocot plants. While Act1 and Ubi1 promoters exhibit a relatively high activity in monocot plants compared to a CaMV 35S promoter, there are drawbacks. For example, the Act1 promoter exhibits activity mainly in vegetative tissue and reproductive tissue, and thus is not effective for expression of a ubiquitous gene in monocot plants. Although the Ubi1 promoter exhibits activity in numerous types of cells, it does not exhibit activity in the substantially all tissues of a plant. Also, while the Ubi1 promoter exhibits a strong activity, especially in young roots, the activity is greatly reduced over time, for example as the root grows.

Accordingly, there is a need for developing a promoter exhibiting a strong, stable and ubiquitous activity in the transformation of plants, including monocot plants. There is a need for suitable promoters useful in the substantially uniform expression of a gene in substantially all the tissues of a plant. There is a need for suitable promoters useful in the production of transformed compositions, and suitable methods for fabricating the same. There is also a need for suitable primers for a variety of novel promoters.

SUMMARY

Embodiments relate to a promoter. In example embodiments, a promoter may include at least one of SEQ ID NO: 1, SEQ ID NO: 2, SEQ ID NO: SEQ ID NO: 4, SEQ ID NO: 5, SEQ ID NO: 6, SEQ ID NO: 7 and SEQ ID NO: 8 (i.e., SEQ ID NO: 1 through SEQ ID NO: 8).

Embodiments relate to a promoter that may be a constitutive expression promoter which is linked to a gene to transform a plant, such as a monocot plant. In example embodiments, a monocot plant may include at east one of a rice, barley, wheat, maize, millet and Indian millet. In embodiments, a promoter may express a gene substantially uniformly in substantially all organs and/or tissues of a plant.

Embodiments relate to a promoter that may include a base sequence complementary to the entire length at least one of SEQ ID NO: 1 through SEQ ID NO: 8. In embodiments, a promoter may include a variant of at least one of SEQ ID NO: 1 through SEQ ID NO: 8. In embodiments, a promoter may include a base sequence complementary to the variant of at least one of SEQ ID NO: 1 through SEQ ID NO: 8.

Embodiments relate to a vector. In example embodiments, a vector may include a promoter consisting of at least one of SEQ ID NO: 1 through SEQ ID NO: 8. In embodiments, a vector may be a recombinant plant expression vector and the promoter may be a constitutive promoter. In embodiments, a target gene downstream of a promoter encoding a target protein may be operably linked. In embodiments, a promoter of a vector may express a gene substantially uniformly in substantially all organs and/or tissues of a plant. In embodiments, a vector may include a variant of at least one of SEQ ID NO: 1 through SEQ ID NO: 8.

Embodiments relate to a transformed plant. In example embodiments, a plant may include a promoter consisting of at least one of SEQ ID NO: 1 through SEQ ID NO: 8. Embodiments relate to a transformed seed. In example embodiments, a seed may include a promoter consisting of at least one of SEQ ID NO: 1 through SEQ ID NO: 20. Embodiments relate to a transformed cell. In example embodiments, a cell may include a promoter consisting of at least one of SEQ ID NO: 1 through SEQ ID NO: 20.

Embodiments relate to a method of forming a target protein. In embodiments, a plant may be transformed using a vector that may include a promoter which may include at least one of SEQ ID NO: 1 through SEQ ID NO: 8. In example embodiments, a target protein may include at least one of interleukin, interferon, platelet-derived growth factor, hemoglobin, elastin, collagen, insulin, fibroblast growth factor, human growth factor, human serum albumin and erythropoietin.

Embodiments relate to a method of transforming a cell and/or plant. In embodiments, a plant cell may be transformed using a vector that may include a promoter which may include at least one of SEQ ID NO: 1 through SEQ ID NO: 8. In example embodiments, a transformed plant may be redifferentiated from a transformed plant cell.

DRAWINGS

The patent or application file contains at least one drawing executed in color. Copies of this patent or patent application publication with color drawing(s) will be provided by the Office upon request and payment of the necessary fee.

DESCRIPTION

Figure 1:
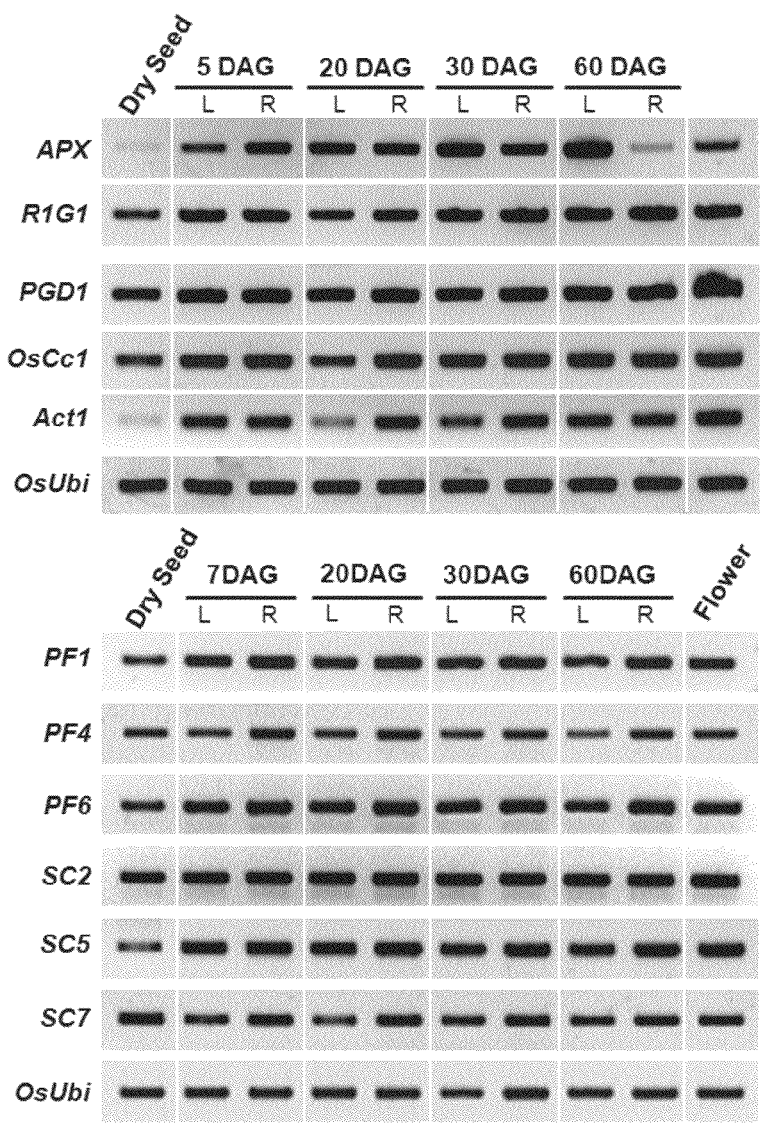
FIG. 1 shows the expression of genes according to embodiments relative to constitutive expression genes (OsCc1, Act1 and Ub1) in various tissues of a plant.

Embodiments relate to a promoter derived from monocot plants, such as rice. In embodiments, the promoter may be suitable for the transformation of plants including monocot plants and may be suitable for the constitutive expression of plant genes. A promoter according to embodiments may express a gene substantially uniformly in substantially all the organs and/or tissues of a plant. In embodiments, a promoter may include at least one of SEQ ID NO: 1 through SEQ ID NO: 8 and may include a base sequence complementary to the entire length of SEQ ID NO: 1 to SEQ ID NO: 8. "Complementary" may relate to hybridization and/or base pairing between nucleotides or nucleic acids, for instance, between two strands of a DNA molecule.

A promoter may relate to a DNA molecule to which RNA polymerase binds in order to initiate transcription and may refer to a DNA region upstream of a structural gene. A plant promoter may relate to a promoter which may initiate transcription in a plant cell. A constitutive promoter may relate to a promoter which may be active in most environmental conditions and/or development states and/or cell differentiation states. Since the selection of a transformant may be carried out by various tissues at various stages, a constitutive promoter may be preferable. However, one is not limited to selecting a constitutive promoter according to embodiments.

In embodiments, a promoter may include at least one of an ascorbate peroxidase (APX) promoter of SEQ ID NO: 1, a putative R1G1 domain containing protein (R1G1) promoter of SEQ ID NO: 2, a PF1 promoter (60S acidic ribosomal protein P1) of SEQ ID NO: 3, a PF4 promoter (40S ribosomal protein S8) of SEQ ID NO: 4, a PF6 promoter (ribosomal protein S26E family protein of SEQ ID NO: 5, an SC2 promoter (historic H3.3) of SEQ ID NO: 6, an SC5 promoter (60S ribosomal protein L9) of SEQ ID NO: 7, and an SC7 promoter (histone H2B.1) of SEQ ID NO: 8.

In embodiments, a promoter may include at least one of SEQ ID NO: 1 through SEQ ID NO: 8 and may be operatively linked to a gene to transform a plant, including a monocot plant, in embodiments, a monocot plant may be, but is not limited to, at least one of a rice, barley, wheat, maize, millet and Indian millet. In embodiments, a promoter may express a gene substantially uniformly in substantially all the organs and/or tissues of a plant, including a monocot plant.

Embodiments relate to variants of a promoter which may include a variant of at least one of SEQ ID NO: 1 through SEQ ID NO: 8. In embodiments, a variant may have different base sequences but include functional characteristics similar to those of at least one of SEQ ID NO 1 through SEQ ID NO: 8. A variant may result from at least one of a substitution, deletion and insertion of nucleic acid base(s), or combinations thereof, including functional fragments thereof. In example embodiments, a base sequence complementary to the variant at least one of SEQ ID NO: 1 through SEQ ID NO: 8 may be included.

In example embodiments, a variant of a promoter may have a sequence identity of at least 70%, preferably at least 80%, even more preferably 90%, and most preferably at east 95% to the at least one of SEQ ID NO: 1 through SEQ ID NO: 8. A percentage of sequence identity to a polynucleotide may be determined by comparing two optimally aligned sequences over a comparison window, wherein the portion of the polynucleotide sequence in the comparison window may include additions or deletions (i.e., gaps) and/or substitutions as compared to the reference sequence (which does not include additions, deletions or substitutions) for optimal alignment of the two sequences.

Substantial identity of polynucleotide sequences may relate to a polynucleotide including a sequence having between 50-100% sequence identity, preferably at least 70% sequence identity, preferably at least 80% sequence identity, snore preferably at least 90%, and most preferably at least 95%. Substantial identity may also relate to when two nucleotide molecules are hybridised specifically to each other under a stringent condition such that their sequences may be substantially identical to each other. For example, stringent condition may vary depending on nucleotide sequences, and thus can be different at a different condition. At certain ionic strength and pH, for example, a stringent condition may be selected to have a temperature that is about 10° C. lower than the heat-melting point (Tm) of a specific sequence. Tm may relate to a temperature at which 50% of a target sequence is hybridized to a fully complementary probe (under the condition of certain ionic strength and pH). For example, a stringent condition for carrying out Southern blot analysis may include washing with 0.2×SSC at 65° C. For an oligonucleotide probe, washing may be carried out with 6×SSC at 42° C.

Embodiments relate to a vector. A vector may relate to a DNA fragment(s) and/or nucleotide molecules delivered to a cell. A vector may replicate DNA and be independently reproduced in a host cell. The terms "delivery system" and "vector" may be interchangeably used. An expression vector may relate to a recombinant DNA molecule including a desired coding sequence and other appropriate nucleotide sequences that are essential for the expression of a coding sequence in a specific host organism, such an operatively-linked coding sequence. The aforementioned other appropriate sequences may include at least one of an promoter, an enhancer, a terminator and a polyadenylation signal that may be suitable for use in a eukaryotic cell. For example, any related terminator may be used according to embodiments. Examples thereof include, but are not limited to, nopaline synthase (NOS), rice α-amylase RAmy1 A terminator, phaseoline terminator, and a terminator for optopine gene of *Agrobacterium tumefaciens*. Since a terminator region may increase the reliability and efficiency of transcription in plant cells, a terminator may be highly preferable.

"Recombinant" may relate to a cell which replicates a heterogeneous nucleotide and/or expresses the nucleotide, a peptide, a heterogeneous peptide, or a protein encoded by a heterogeneous nucleotide. A recombinant cell may express a gene or a gene fragment in a sense or antisense form, which are not found in the natural state of the cell. Embodiments relate to a vector which may be a recombinant vector.

Embodiments relating to vectors which may be used to introduce DNA into a plant host may include viral vectors, for example, non-integrative plant viral vectors, such as derivable from the double stranded plant viruses (for example, CaMV) and single stranded viruses, gemini viruses and the like. The use of such vectors may be preferable, particularly when it is difficult to stably transform a plant host.

Embodiments relating to vectors may preferably include at least one selective marker. A selective marker may relate to a nucleotide sequence having a property which allows selection based on a common chemical method. It may be any kind of gene that may be used for the differentiation of transformed cells from non-transformed cell. Examples thereof include, but are not limited to, herbicide-resistant genes, such as glyphosate or phosphintricin, and antibiotic-resistant genes, such as kanamycin, G418, bleomycin, hygromycin or chloramphenicol.

In example embodiments, a recombinant plant expression vector may include a Ti-plasmid vector that, when present in a suitable host, such as *Agrobacterium tumefaciens*, is capable of transferring part of itself, the so-called T-region, to a plant cell. Embodiments include different types of Ti-plasmid vectors, for example those disclosed in EP 0 116 718, to transfer chimeric DNA sequences into plant cells, or protoplasts, from which new plants may be generated which stably incorporate said chimeric DNA in their genomes. Particularly preferred forms of Ti-plasmid vectors are the so-called binary vectors as described in EP No. 0 120 516 B1 and U.S. Pat. No. 4,940,838.

In embodiments, a vector may be a recombinant plant expression vector including a promoter in accordance with embodiments. An example of the recombinant plant expression vector may be, but is not limited to, a vector shown in FIG. 2. As shown in the example embodiment of FIG. 2, a modified green fluorescent protein (GFP), a protease inhibitor II terminator gene ($T_{PINII}$), an OsCc1 promoter (Pcytc), a herbicide-resistant gene Bar (phosphinotricine acetyltransferase gene) and a nopaline synthase terminator ($T_{NOS}$) may be operably linked to a promoter according to embodiments. Also as shown in the example embodiment of FIG. 2, a MAR sequence may be attached to the terminal of the right-border sequence. In embodiments, the aforementioned attachment may minimize the change in expression in the chromosome in various sites of the chromosome such that only the inherent activity of the promoter according to embodiments can be measured.

In embodiments a vector, such as recombinant plant expression vector, may be prepared by operably linking a target gene encoding a target protein downstream of a promoter according to embodiments. "Operably linked" may relate to the element of an expression cassette which functions as a unit to express, for example, a heterogeneous protein. In example embodiments, a promoter that may be operably linked to a heterogeneous DNA which may encode a protein may promote the production of functional mRNA corresponding to the heterogeneous DNA.

In embodiments, a target protein may be any kind of protein, and examples thereof include, but are not limited to, proteins having medical utility, such as enzymes, hormones, antibodies or cytokines, and proteins which can accumulate large amounts of nutrients capable of improving the health of animals including humans. Example embodiments of a target protein include, but are not limited to, interleukin, interferon, platelet-derived growth factor, hemoglobin, elastin, collagen, insulin, fibroblast growth factor, human growth factor, human serum albumin and erythropoietin.

Embodiments relate to a method of producing a target protein. In embodiments, the target protein may be produced by transforming plant using a vector including a promoter in accordance with embodiments. In example embodiments, the target protein may be produced by constitutive expression in a plant and may include transforming a plant with a recombinant plant expression vector. Embodiments of a target protein are described hereinabove.

According to embodiments, plant transformation may refer to any method of introducing DNA is into a plant. Such transformation methods do not necessarily have a period for regeneration and/or tissue culture. In embodiments, transformation of a plant species is possible for dicot plants and for monocot plants. In embodiments, any transformation method can be used to introduce a hybrid DNA according to embodiments to a suitable ancestor cells. Example methods include a calcium/polyethylene glycol method for protoplast transformation, electroporation of protoplasts, microinjection into plant material, (DNA or RNA-coated) particle bombardment of various plant materials, gene gun methods, infection with (non-integrative) viruses, in planta *Agrobacterium tumefaciens*-mediated gene transfer by infiltration of adult plants or transformation of mature pollen or microspores (EP 0 301 316) and the like. A preferred method according to embodiments may include *Agrobacterium*-mediated DNA transfer. More preferably, use of a so-called binary vector technology, disclosed in EP A 120 516 and U.S. Pat. No. 4,940,838, may be used.

According to embodiments, a plant cell that may be used in plant transformation may be any plant cell. A plant cell may be a cultured cell, a cultured tissue, a cultured organ or a whole plant, and may preferably be a cultured cell, a cultured tissue or a cultured organ, and most preferably a cultured cell according to embodiments. Plant tissue may relate to a differentiated or undifferentiated plant tissue. Embodiments of a plant tissue include, but are not limited to, root, stem, leaf, pollen, seed, cancerous tissue, and cells of various shapes that are used in culture, namely, single cells, protoplasts, buds and callus tissues. In embodiments, a plant tissue may be in planta or in organ culture, tissue culture or cell culture.

Embodiments relate to a method of producing a transformed cell and/or plant. In embodiments, the method may include transforming a plant cell with a vector including a promoter according to embodiments, and may include differentiating a transformed plant from a transformed plant cell. In example embodiments, a recombinant plant expression vector may be used. In example embodiments, the plant transformation may be mediated by, for example, *Agrobacterium tumefaciens*. In example embodiments, redifferentiation of the transformed plant from the transformed plant cell may be carried out using any related method in the art.

Embodiments relate to a transformed plant, which may be produced by the above-described method. The plant may preferably be, but is not limited to, a monocot plant, and more preferably may be rice, barley, wheat, maize, millet or Indian millet. Embodiments relate to a transformed seed. In embodiments, the transformed seed may be obtained from a transformed plant. A seed preferably may be derived from, but is not limited to, a monocot plant, and more preferably may be from rice, barley, wheat, maize, millet or Indian millet. Embodiments relate to a transformed cell. In embodiments, the transformed may be obtained a transformed plant. A cell preferably may be derived from, but is not limited to, a monocot plant, and more preferably may be from rice, barley, wheat, maize, millet or Indian millet.

Hereinafter, the present invention will be described in further detail with reference to example embodiments. It is to be understood, however, that these examples are for illustrative purposes only and are not to be construed to limit the scope of the present invention.

1. Embodiment of Selection and Extraction of Promoter Sequences.

Using the rice genome sequences of the international rice genome sequencing project (IRGSP), which was established in 1997 and completed the sequencing of the rice genome in December, 2004, and gene annotation data from the Institute for Genomic Research (TIGR) which carried out gene annotation based on the rice genome sequences, a region was selected to investigate its activity in a transformation, for example its activity in a vector. An annotated bacterial artificial chromosome (BAC) was selected, and about 2 kbp of sequence upstream from a ATG start codon of a coding sequence (CDS) was selected to be investigated as a promoter region. Only the 2-kbp sequence was extracted, separately, and used as a template for constructing PCR primers for isolating about 1.7-2-kb promoters from the 2-kbp sequence.

2. Embodiment of Analysis of a Constitutive Expression Gene by RT-PCR.

For the analysis of a constitutive expression gene, samples were collected from seeds and leaf, root and flower tissues of 5-day-old (or 7-day-old), 2d-day-old, 30-day-old and 60-day-old seedlings. For the preparation of the samples, the seeds were disinfected with about 70% ethanol and about 20% chlorax solutions, grown in a dark condition for about 5 days, and then developed in a greenhouse. To extract the RNA, an RNeasy plant mini-kit (Qiagen, Cat. No. 74904) was used. A first-strand cDNA was synthesized using about 400 ng of the extracted total RNA (Invitrogen, Cat. No. 18080-051), and PCR was performed using about 1 μl of the synthesized cDNA product as a template. The primers used in the PCR reaction were as follows, and an ubiquitin (Ubi) primer set was used as a cDNA loading control.

```
Forward primer APX:
                                       (SEQ ID NO: 9)
5'-GACCTCTAGACCGCCGTATT-3'

Reverse primer APX:
                                       (SEQ ID NO: 10)
5'-GCCAACCACTCGCAATCCAA-3'

Forward primer R1G1:
                                       (SEQ ID NO: 11)
5'-CTTCTCGATTGCCGTGTGCT-3'

Reverse primer R1G1:
                                       (SEQ ID NO: 12)
5'-GCAAGTCTCAAGCTCTCAAT-3'

Forward primer PF1:
                                       (SEQ ID NO: 13)
5'-GGTCTCTTCGCCAAGCTCCT-3'

Reverse primer PF1:
                                       (SEQ ID NO: 14)
5'-CGCCTCCTCCTTCTTCTCCT-3'

Forward primer PF4:
                                       (SEQ ID NO: 15)
5'-CAATGTGGCAGAGCTGATGG-3'

Reverse primer PF4:
                                       (SEQ ID NO: 16)
5'-GGTCTGTAGGCACGACATAG-3'

Forward primer PF6:
                                       (SEQ ID NO: 17)
5'-GAAGCTGTACGCCAAGGT-3'

Reverse primer PF6:
                                       (SEQ ID NO: 18)
5'-TAGGTGCGAGCAACATTAGG-3'

Forward primer SC2:
                                       (SEQ ID NO: 19)
5'-CTGCGGAGGCATACCTTGTT-3'

Reverse primer SC2:
                                       (SEQ ID NO: 20)
5'-ACACTACGACGCATGCTTCA-3'

Forward primer SC5:
                                        SEQ ID NO: 21)
5'-CATCTTGCGGTCGGAGAA-3'

Reverse primer SC5:
                                       (SEQ ID NO: 22)
5'-TACGCATCCTCTGTGATGGT-3'

Forward primer SC7:
                                       (SEQ ID NO: 23)
5'-CGTCACCAAGTTCACTTC-3'

Reverse primer SC7:
                                        SEQ ID NO: 24)
5'-CCACCTAATTCTTCTTACAGTC-3'

Forward primer PGD1:
                                       (SEQ ID NO: 25)
5'-CCGTGAGCTAGCGAGGATCT-3'

Reverse primer PGD1:
                                       (SEQ ID NO: 26)
5'-CCGGTAGGAGTCGAAGTACG-3'

Forward primer OsCc1:
                                      (SAEQ ID NO: 27)
5'-ACTCTACGGCCAACAAGAAC-3'

Reverse primer OsCc1:
                                       (SEQ ID NO: 28)
5'-CTCCTGTGGCTTCTTCAACC-3'
```

```
Forward primer Act1:
                                        (SEQ ID NO: 29)
5'-ATGGTGTCAGCCACACTGTC-3'

Reverse primer Act1:
                                        (SEQ ID NO: 30)
5'-TAACCACGCTCCGTCAGGAT-3'

Forward primer OsUbi:
                                        (SEQ ID NO: 31)
5'-ATGGAGCTGCTGCTGTTCTA-3'

Reverse primer OsUbi:
                                        (SEQ ID NO 32)
5'-TTCTTCCATGCTGCTCTACC-3'
```

The PCR reaction was performed in a PTC 200 PCR machine (MJ research) using about 1 µl of cDNA, 2× Taq premix (Solgent. Co. Cat. No. EP051020-T2B6-1), about 4 pmol of each template-specific primer in a total reaction volume of about 20 µl for about 32 cycles, each consisting of about 95° C. for about 30 sec, about 55° C. for about 30 sec and about 72° C. for about 1 min.

3. Embodiments of Amplification and Isolation of Promoters.

Using the isolated 2-kbp promoter sequence as a template and a primer designer 4 program (ver. 4.20, Scientific & Educational software), PCR primers for isolating about 1.8-2-kb promoters were designed. The design conditions were as follows: the GC content of PCR primers: about 40-60%, Tm: about 55-65° C., and the concentrations of salt and free Mg: about 0 and about 0.15 mM, respectively. The primers (PCR primers) were designed such that the template-specific region was about 20 bp in length and the 5' adaptor sequence was about 12 bp in length. The adaptor sequence was inserted for site-specific recombination other than existing cloning methods which are performed using restriction enzymes and DNA ligase. DNA used as a template was obtained by seeding a Japonica type Nipponbare cultivar rice, growing the plant in a greenhouse for about 3 weeks, cutting only the leap portion from the plant, and extracting genomic DNA from the leaf. The genomic DNA was obtained by freezing the cut leaf rapidly with liquid nitrogen, crushing the frozen leaf finely with a mortar and pestle, and then isolating the genomic DNA from the crushed leaf using DNAzol solution (molecular research center, Cat. No. DN128). The first reaction was carried out to isolate a specific promoter from the rice genome and performed using 32-bp template-specific primers linked with a 2-bp adaptor sequence. The primer sequences were as follows:

```
Forward template-specific primer:
5'-AAAAAGCAGGCT-tempate specific sequence-3'

Reverse template-specific primer:
5'-AGAAAGCTGGGT-template specific sequence-3'
```

Embodiments of gene-specific primer sequences were as follows:

a. APX Promoter Primers

```
Forward primer:
                                        (SEQ ID NO: 33)
5'-AAAAAGCAGGCTgtaaggtgacatggcatatc-3'

Reverse primer:
                                        (SEQ ID NO: 34)
5'-AGAAAGCTGGGTccaatccgaatcaatcaatc-3'
``` b. R1G1 Promoter Primers

```
Forward primer:
                                        (SEQ ID NO: 35)
5'-AAAAAGCAGGCTatagctgttgtactgatgtc-3'

Reverse primer:
                                        (SEQ ID NO: 36)
5'-AGAAAGCTGGGTtctctcgcagtattaccaac-3'
``` c. PF1 Promoter Primers

```
Forward primer:
                                        (SEQ ID NO: 37)
5'-AAAAAGCAGGCTctcggtgaagatagagaagg-3'

Reverse primer:
                                        (SEQ ID NO: 38)
5'-AGAAAGCTGGGTctcgagctgatctacgaact-3'
``` d. PF1 Promoter Primers

```
Forward primer:
                                        (SEQ ID NO: 39)
5'-AAAAAGCAGGCTtctggcatcgatatgctcct-3'

Reverse primer:
                                        (SEQ ID NO: 40)
5'-AGAAAGCTGGGTtggagtcacgcgagatacct-3'
``` e. PF6 Promoter Primers

```
Forward primer:
                                        (SEQ ID NO: 41)
5'-AAAAAGCAGGCTggaccaaccgaagtccttcc-3'

Reverse primer:
                                        (SEQ ID NO: 42)
5'-AGAAAGCTGGGTtcctgcgcttgaaggtct-3'
``` f. SC2 Promoter Primers

```
Forward primer:
                                        (SEQ ID NO: 43)
5'-AAAAAGCAGGCTttacgtatagccttttcctt-3'

Reverse primer:
                                        (SEQ ID NO: 44)
5'-AGAAAGCTGGGTgacagaatatgctgtgacaa-3'
``` g. SC5 Promoter Primers

```
Forward primer:
                                        (SEQ ID NO: 45)
5'-AAAAAGCAGGCTtcctcttgccccttcctcgg-3'

Reverse primer:
                                        (SEQ ID NO: 46)
5'-AGAAAGCTGGGTtgtgacgtggcagtctgaca-3'
``` h. SC7 Promoter Primers

```
Forward primer:
                                        (SEQ ID NO: 47)
5'-AAAAAGCAGGCTgtcgaactcaccgtgcacta-3'

Reverse primer:
                                        (SEQ ID NO: 48)
5'-AGAAAGCTGGGTtggatgctgctctcttcttctc-3'
```

A first PCR reaction was carried out using about 50 ng of genomic DNA, 2× Taq premix (Solgent. Co. Cat. No. EP051020-T2B6-1) and about 10 pmol of each template-specific primer in a total reaction volume of about 50 μl for about 30 cycles, each consisting of about 95° C. for about 1 min, about 55° C. for about 1 min and about 68° C. for about 2 min.

A second PCR reaction was carried to insert and amplify a specific adaptor sequence (att site) which may be used to insert a promoter into a transformation vector. The length of the sequence to be additionally inserted into the promoter was about 29 bp. To increase the efficiency of PCR, only a portion (12 bp) of the sequence was attached to the template-specific sequence by overhang and subjected to the first PCR reaction. Then, about 1/50 (1 μl) of the PCR reaction solution was taken and subjected to the second PCR reaction using primers (adaptor sequence primers) having full-length recombinant sequences. Thus, the PCR product had all the att sequences for recombination with the promoter. The adaptor primer sequences were as follows:

```
attB1 adaptor primer:
                                    (SEQ ID NO: 49)
5'-GGGGACAAGTTTGTACAAAAAAGCAGGCT-3' attB2 adaptor primer:
                                    (SEQ ID NO: 50)
5'-GGGGACCACTTTGTACAAGAAAGCTGGGT-3'
```

The second PCR reaction was carried out using about 1 μl of the first PCR product, 2× Taq premix (Solgent. Co. Cat. No. EP051020-T2B6-1) and about 2 pmol of each adaptor primer in a total reaction volume of about 50 μl for about 5 cycles, each consisting of about 95° C. tier about 30 sec, about 45° C. for about 30 sec and about 68° C. for about 2 min, followed by about 20 cycles, each consisting of about 95° C. for about 30 sec, about 55° C. for about 30 sec and about 68° C. for about 2 min. The PCR reactions were carried out using a Gateway system (invitrogen, Cat. No. 12535-029) according to the method suggested by Invitrogen.

4. Embodiments of Cloning of Amplified Promoters.

The promoter was inserted into a vector using a Gateway system (Invitrogen Cat. No. 12535-029). The amplified promoter was electrophoresed on about 1% agrose gel, separated into bands on the gel and purified using the Mega-spin agarose gel extraction kit (Intron, Cat. No. 17183). A BP reaction was carried out using about 5 μl of the purified promoter, about 4 μl of a BP clonase enzyme mixture, about 4 μl of 5×BP reaction buffer, about 300 ng/2 μl of a pDONR vector, and TE buffer (about 10 mM Tris/pH about 8.0, about 1 mM EDTA) in a total reaction volume of about 20 μl at about 25° C. for about 16 hours. Then, about 6 μl of an LR clonase enzyme mixture, about 1 μl of about 0.75 M NaCl and about 450 ng/3 μl of a transformation vector were added to the reaction product and subjected to an LR reaction in a total reaction volume of about 30 μl at about 25° C. for about 8 hours. About 3 μl of proteinase was added thereto and allowed to react at about 37° C. for about 1 hour, and then about 2 μl of the reaction product was taken and transformed into DH5α competent cells. The transformed DH5α cells were plated in LB agar medium containing about 50 μg/ml of a Spectinomycin antibiotic and were grown in an incubator at about 37° C. for about 12 hours. DNA was extracted from the selected cells, and whether the promoter has been inserted into the extracted DNA was confirmed by PCR. Then, the DNA was subjected to sequencing and BLASTN analysis to confirm complete insertion of the isolated promoter.

A vector (pMJ401) is described as follows. Between the right-border sequence and the left-border sequence, a cassette to be replaced with a promoter according to embodiments subsequent to recombination is linked with the visible marker gene GFP and a protease inhibitor II at the 3' end. The cassette has the att sequences to facilitate BP and LR reactions. The selection gene (selection marker gene) was prepared such that the herbicide-resistant gene bar (phosphinotricine acetyltransferase gene) was controlled by the constitutive expression promoter OsCc1 (see U.S. Pat. No. 6,958,434). The gene was linked with a nopalin synthase (NOS) terminator. Also, a MAR sequence was attached to the terminal of the right-border sequence to minimize the change in expression in various sites of the chromosome, such that only the inherent activity of the promoter could be measured.

5. Embodiments of *Agrobacterium*-Mediated Transformation of Rice.

About 70% (v/v) ethanol was added to T0 hulled rice seeds (*Oryza sativa* L. cv *Nakdong*) and gently mixed for about 1 minute to wash the seeds. The washed seeds were sterilized by treatment in about 20% chlorax for about 1 hour and washed several times with sterile water. For transformation, the washed rice seeds were incubated on a callus induction medium (2N6) for about one month according to the method of Jang et al (Jang, I-C. et al., Mol breeding, 5:453-461, 1999) to induce embryonic callus, and then were co-cultivated with *Agrobacterium* obtained by an *Agrobacterium* triple mating method so as to insert the promoter-inserted transformation vector into the rice genome. Then, the plant was incubated on a 2N6-CP medium for selecting transformed callus for about one month. The grown cells were selected and cultured in a redifferentiation medium (MS-CP) for about 1-2 months, and a redifferentiated plant was acclimated in a greenhouse. The acclimated T0 rice was treated with the non-selective herbicide basta, and only the plants showing herbicide resistance were selected and subjected to a progeny test.

6. Embodiments of Analysis of Promoter Activity by RT-PCR and Real Time qRT-PCR

For the analysis of promoter activity, total RNA was extracted from the seeds of transformed plants and the leaf, root and flower tissues of 5-day-old, 20-day-old, 30-day-old and 60-day-old seedlings. An RNeasy plant mini-kit (Qiagen, Cat. No. 74904) was used to extract the total RNA from each tissue. A first-strand cDNA was synthesized using about 400 ng of the extracted total RNA (Invitrogen, Cat. No. 18080-051), and PCR was performed using about 1 μl of the synthesized cDNA product as a template. The PCR reaction was performed using two kinds of primer sets. The first primer set was a primer set (primer GFP) for comparing the expression levels of GFP inserted downstream of the promoters, and the second primer set was a primer set (primer Ubi) as a cDNA loading control. The primer sequences were as follows.

```
Forward primer GFP:
                                    (SEQ ID NO: 51)
5'-CAGCACGACTTCTTCAAGTCC-3'

Reverse primer GFP:
                                    (SEQ ID NO: 52)
5'-CTTCAGCTCGATGCGGTTCAC-3'

Forward primer OsUbi:
                                    (SEQ ID NO: 53)
5-ATGGAGCTGCTGCTGTTCTA-3'

Reverse primer OsUbi:
                                    (SEQ ID NO: 54)
5'-TTCTTCCATGCTGCTCTACC-3'
```

The RT-PCR reaction was carried out in a PTC 200 PCR machine (MJ research) using about 1 μl of cDNA, 2× Taq premix (Solgent. Co. Cat. No. EP051020-T2B6-1) and about 2 pmol of each template-specific primer in a total reaction volume of about 20 μl for about 39 cycles, each consisting of about 95° C. for about 30 sec, about 55° C.; for about 30 sec and about 72° C. for about 30 sec.

The real-time qRT-PCR reaction was carried out in Mx3000P (Stratagene) using about 1 μl of cDNA, 2×SYBR green qRT-PCR premix (Invitrogen. Cat. No. 11765-100) and about 2 pmol of each template-specific primer in a total reaction volume of about 20 μl for about 40 cycles, each consisting of about 95° C. for about 15 sec and about 60° C. for about 30 sec. After completion of the reaction, the promoter activity was quantitatively analyzed using the program Mx3000P (Stratagene) according to the manufacture instruction.

7. Embodiments of Observation of GFP Expression and Analysis of Promoter Activity in Each Organ of Rice.

GFP fluorescence in different regions of the leaves and roots of 7 days after germination (DAG) rice plants was visualized and photographed using a confocal laser scanning microscope (Carl Zeiss LS410 CLSM, Jena, Germany). Pseudo-color, similar to the color observed under a fluorescence microscope, was added to the images by importing data collected in the green and red channels of the confocal microscope. Sections along the optical axis were prepared and projected into a single image. The other regions were observed using a research stereomicroscope (SZX9-3122, Olympus, Tokyo, Japan) equipped with an attachment for fluorescence observations. Images were captured using a C5060-ZOOM digital camera (Olympus). Observations under blue light were carried out using a specific filter set (460-480 nm excitation filters, dichroic mirrors of 485 nm and a 495-540 nm barrier filter).

8. Embodiments of Immunoblotting Analysis

Total soluble proteins were extracted from 30-day-old leaves, roots and flowers. The extraction buffer consisted of 20 mM Tris-Cl, pH 8.0, 10 mM EDTA pH 8.0, 30 mM NaCl and 100 μM phenylmethylsulphonylfluoride (PMSF). The extracts were centrifuged at 9,000 g at 4° C. for 30 min and protein concentrations were determined using the Bradford method (Bio-Rad, Hercules, Calif.). Protein extracts were then separated on 12% SDS polyacrylamide gels and blotted onto a polyvinylidenedifluoride (PVDF) membrane (Immobilon-P, Millipore Co., Billerica, Mass.) using a semi-dry transfer apparatus (Hoefer, Inc., San Francisco, Calif.). The immunoreactive proteins were detected using primary antibodies against GFP (Nacalai Tesque, Inc., Kyoto). The chemiluminescence signals generated by the bound antibodies were detected using the Pierce Super Signal Substrate (Pierce, Rockford, Ill.) according to the manufacturer's protocol. Recombinant GFP proteins were used as a positive control (Abcam, Cambridge, UK).

Example 1

Analysis of Expression of Genes in Each Rice Tissue

To examine the tissue-specific activities of the APX and R1G1 promoters, samples were collected from the seeds of the transformed rice and the leaf (L in FIG. 1), root (R in FIG. 1) and flower tissues of 5-day-old (or 7-day-old), 20-day-old, 30-day-old and 60-day-old seedlings, and total RNA was extracted from each sample. cDNA was synthesized using the RNA as a template and amplified by PCR. The PCR products were electrophoresed on about 2% agarose gel.

FIG. 1 shows the results obtained by comparing the expression patterns of eight constitutive expression genes in various tissues of rice using RT-PCR. As can be seen in FIG. 1, APX, R1G1, PF1, PF4, PF6, SC2, SC5 and SC7 genes used in the present invention were expressed substantially uniformly in various tissues of rice. Also, these genes showed expression patterns similar to those of related constitutive expression genes OsCc1 and Act1, suggesting they may be constitutive expression genes.

Example 2

Construction of Rice Transformation Vector and Structure of Promoter

Figure 2:
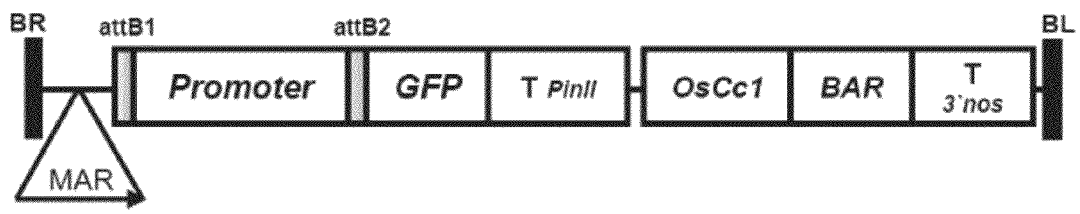
FIG. 2 is a schematic diagram of a vector according to embodiments.

A vector for analyzing promoter activity was constructed and is shown in FIG. 2. FIG. 2 shows a pMJ401 vector. The vector may be a parent vector for cloning the isolated promoter by PCR. The attR11 and attR2 sites are sites where recombination (site-specific recombination) with the attL1 and attL2 sequences of the promoter may occur after a BP reaction. After an LR reaction, a cassette was replaced with the promoter, and the attR1 and attR2 sequences were also replaced with attB1 and attB2 sequences.

Figure 3:
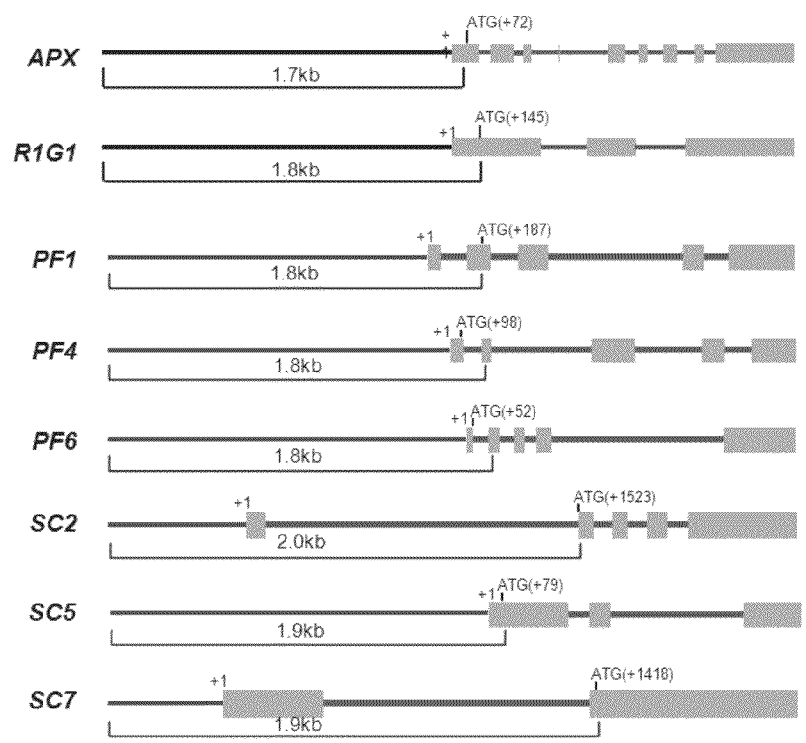
FIG. 3 shows structures of promoters according to embodiments.

A description is provided as follows: MAR: matrix attachment region (1.3 kb), X98408; cassette B: conversion cassette B (1.7 kb; Invitrogen, Cat. No. 11828-019); GFP: modified green fluorescent protein gene (0.74 kb), U84737; TPINII: protease inhibitor II terminator (1.0 kb), X04118; OsCc1: cytochrome c promoter (0.92 kb), Af399666; BAR: phosphinotricine acetyltransferase gene (0.59 kb), X17220; and TNOS: nopaline synthase terminator (0.28 kb). FIG. 3 shows the structures of embodiments of promoters disposed in a rice genome.

Example 3

Figure 4:
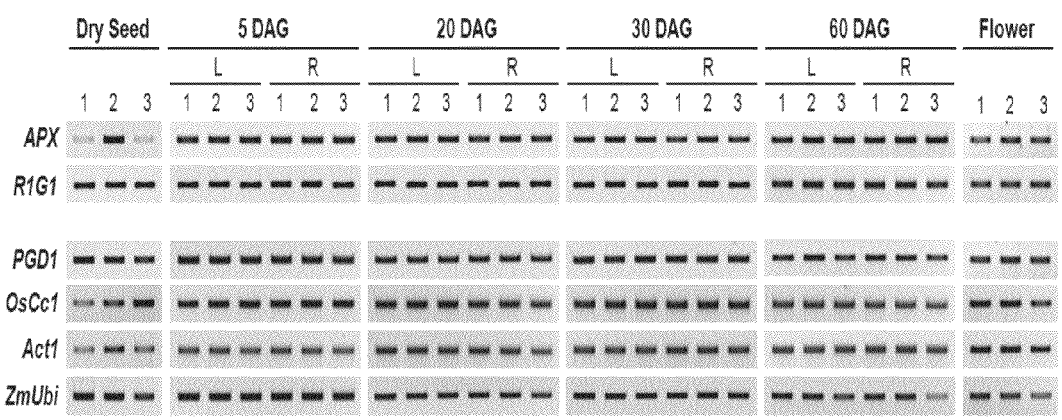
FIG. 4 shows results obtained by observing the expression levels of Green Fluorescent Protein(GFP) in seeds of transformed plant according to embodiments as well as the leaf and root tissues of 5-day-old, 20-day-old and 30-day-old the plants.

Analysis of Promoter Activity GFP Expression Level in Each Tissue of Transformed Rice by RT-PCR RNA was extracted from the seeds of the transformed rice and the leaf root and flower tissues of 5-day-old, 20-day-old, 30-day-old and 60-day-old seedlings. cDNA was synthesized using the RNA as a template and amplified by PCR. The PCR products were electrophoresed on about 2% agarose gel. Each PCR product was loaded in an amount of about 5 μl. FIG. 4 shows the results obtained by semi-quantitatively analyzing the GFP expression level caused by each promoter in the rice seeds and the leaf (L), root (R) and flower tissues of 5-day-old, 20-day-old, 30-day-old and 60-day-old seedlings using RT-PCR. GFP was a PCR product amplified with GFP primers and was used to compare the expression levels of the GFP gene inserted downstream of the promoters. The PCR product was 141 bp in size. In view of the difference in gene expression according to the variation between events, the analysis of the transformants for each promoter was carried out using 3 events having different promoter insertion sites.

FIG. 4 illustrated that, for example, APX and R1G1 promoters were novel promoters, which showed gene expression levels similar to or lower than those of the related PGD1 promoter, OsCc1 promoter, Act1 promoter and maize Ubi1 promoter (ZmUbi), but induced gene expression substantially uniformly in substantially all the tissues.

Example 4

Analysis of Promoter Activity in Each Rice Tissue by Real Time qRT-PCR

Figure 5:
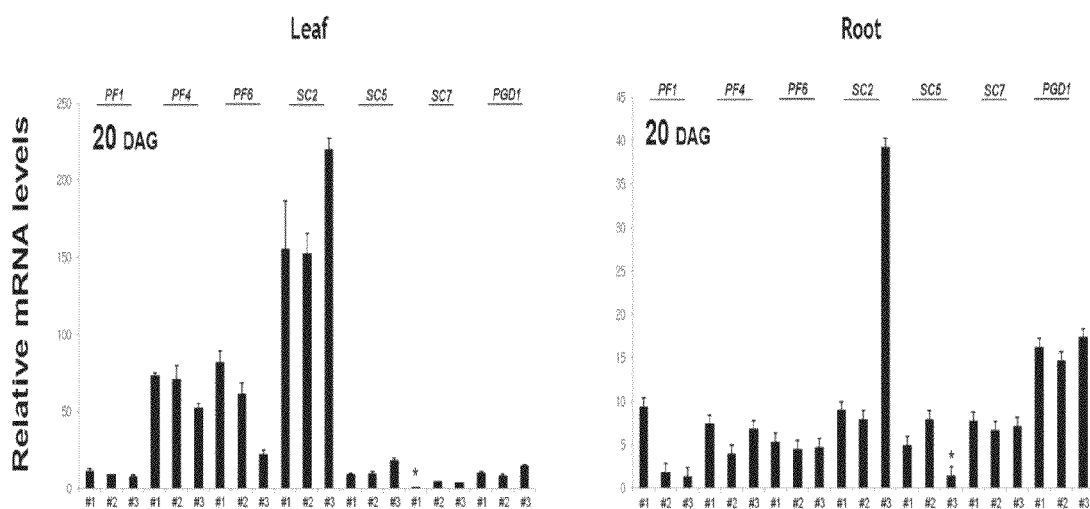
FIG. 5 shows results obtained by quantitatively comparing the expressions of GFP in the leaf and root issues of 20-day-old the plants according to embodiments.

FIG. 5 shows the results obtained by quantitatively analyzing the expression pattern of the GFP gene according to the activity of each promoter in each tissue of the transformed rice. Similar to in FIG. 4, RNA was extracted from the seeds of the transformed rice and the leaf an root tissues of 20-day-old seedlings. cDNA was synthesized using RNA as a template and amplified by PCR. Then, the PCR product was subjected to real time qRT-PCR analysis using gene-specific primers of GFP used as a target gene. In view of the difference in gene expression according to the variation between events, the analysis of the transformants for each promoter was carried out using 3 events having different promoter insertion sites.

FIG. 5 shows the results obtained by quantitatively analyzing the expression pattern of the GFP gene according to the activity of each promoter in each tissue of the transformed rice. This shows that the activities of the promoters according to the present invention were distributed uniformly in the transformed rice plants in the same manner as in the case of the rice plants transformed with each of the positive control, PGD1.

Example 5

Comparison of Exogenous Promoter Activities Over Three Homozygous Generations

Figure 6:
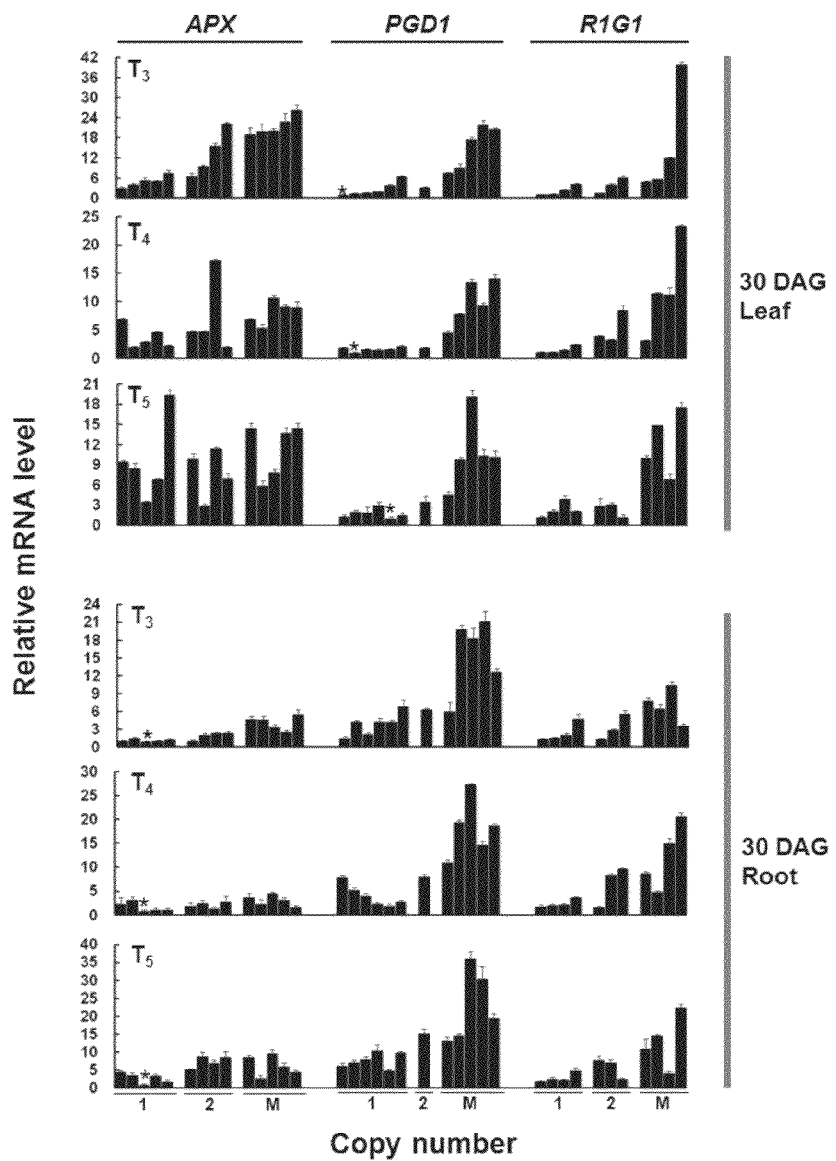
FIG. 6 shows changes in the analyzed promoter activities during three successive generations ($T_3$-$T_5$) according to embodiments.

To investigate whether significant changes occur in the exogenous APX, R1G1 and PGD1 promoter activities over sequential generations in transgenic rice, we measured the respective gfp mRNA levels of $T_3$, $T_4$ and $T_5$ homozygous lines by real-time qPCR using 30 DAG leaf and root tissues. The relative activities among different lines remained similar within each generation (FIG. 6) and the patterns observed in the $T_3$ generation, i.e. that the activity levels of the APX and R1G1 promoters continued to be higher in the leaves and roots, were also observed in the and $T_4$ and $T_5$ generations.

Example 6

Figure 7:
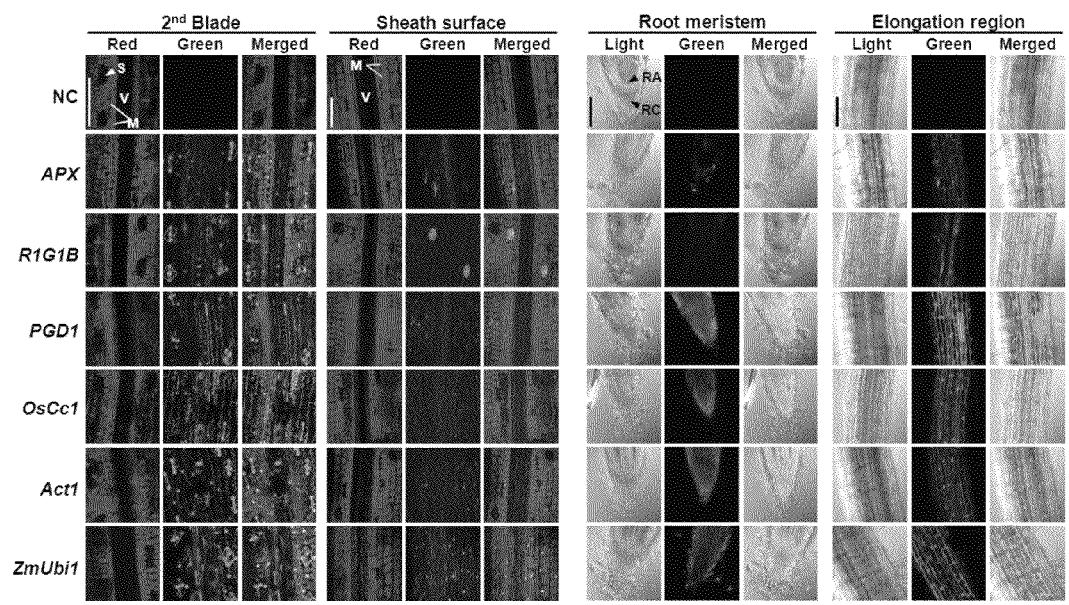
FIGS. 7 and 8 show the expression of GFP fluorescence in the leaf and root of transformed plant according to embodiments.
Figure 8:
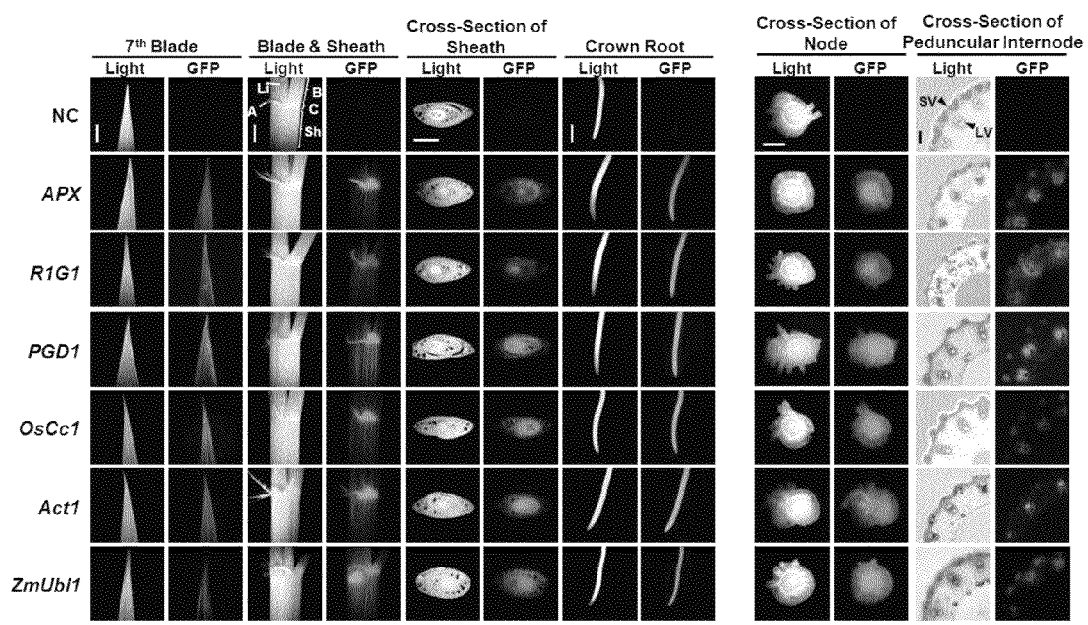
Figure 9:
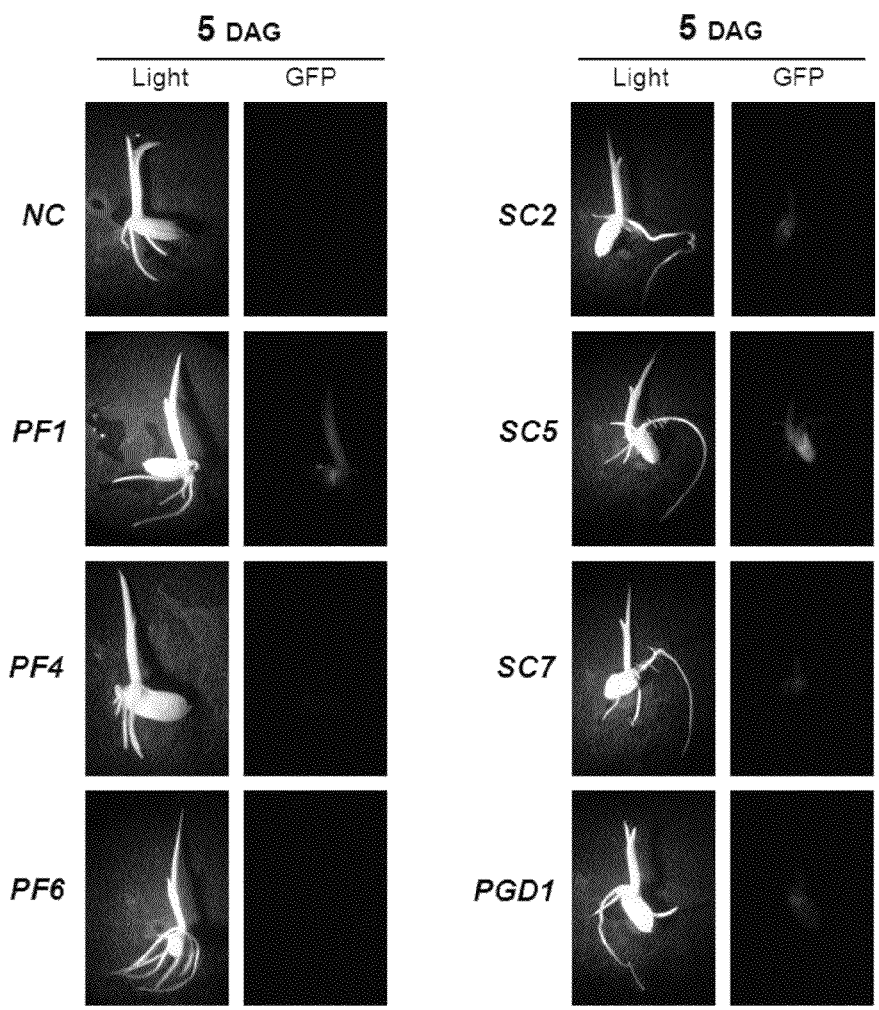
FIG. 9 shows the expression of GFP fluorescence in seedlings of transformed plant according to embodiments.

Observation of GFP Fluorescence in Leaf and Root Tissues of Rice Transformed with Promoter Gene promoter activities in different tissues and/or stages in transgenic rice plants were examined using confocal laser scanning and a fluorescence microscope (FIG. 7). In 7 DAG (days after germination) plants, the levels of GFP fluorescence were high in the vascular bundle sheath and stomatal guard cells, but relatively low in mesophyll cells of the APX: gfp, PGD1:gfp and R1G1:gfp leaves. Levels of GFP fluorescence in root apex, root cap and elongating regions of PGD1: gfp roots were comparable with those of OsCc1, Act1 and ZmUbi1:gfp roots. In contrast, the levels of GFP fluorescence in the corresponding tissues of APX:gfp and R1G1:gfp roots were markedly lower than the others (FIG. 7). We also examined several further tissues at the vegetative stage in promoter:gfp plants. These included the tip of the seventh leaf blade, an area between a leaf blade and a leaf sheath containing the ligule, auricle and collar, a central part of a sheath, and a crown root below a root node (FIG. 8). All three promoters produced. GFP fluorescence at high levels in these additional issues at a similar level to the control promoters (FIG. 8). Stems can be divided into two parts, unelongated and elongated. A region from the node to the nearest crown root of 30 DAG plants representing the unelongated stem showed high levels of GFP fluorescence of the promoter:gfp plants examined. A peduncular internode, the longest uppermost internode, is representative of the elongated stem located just below the panicle inflorescence. Large and small vascular bundle (LV and SV, respectively) sheath cells of the peduncular internode also showed high levels of GFP fluorescence in all of the promoter:gfp plants (FIG. 8). To analyze the activities of the promoters used in the present invention, the 5-day-old seedlings of rice plants transformed with each of the promoters (PF1, PF4, PF6, SC2, SC5, and SC7) and GFP fluorescence in the tissues was observed (FIG. 9).

The description of each gene shown in FIG. 7-8 is as follows: V: vascular bundle sheath; S; stomatal guard cells; M: mesophyll cells; RA: root apex; RC: root cap A: auricle; B: base of the leaf blade; C: collar; LI: ligule; Sh: leaf sheath; LV: large vascular bundle; SV: small vascular bundle; NC: negative control Oryza sativa L. cv Nakdong (non-transformed rice): ZmUbi: maize Ubi1 promoter; Act1: rice Actin1 promoter; and OsCc1: rice cytochrome c promoter.

In the leaf and root tissue of the negative control, the expression of GFP fluorescence was not observed, whereas in the leaf and root tissues of the rice plants transformed with the promoters, the expression of GFP fluorescence was clearly and uniformly observed.

This visually shows that the activities of the constitutive expression promoters of the present invention were distributed uniformly in the leaf and root tissues of the transformed rice plants in the same manner as in the case of the rice plants transformed with each of the positive controls, PGD1, ZmUbi, Actin1 and OsCc1.

Example 7

Figure 10:
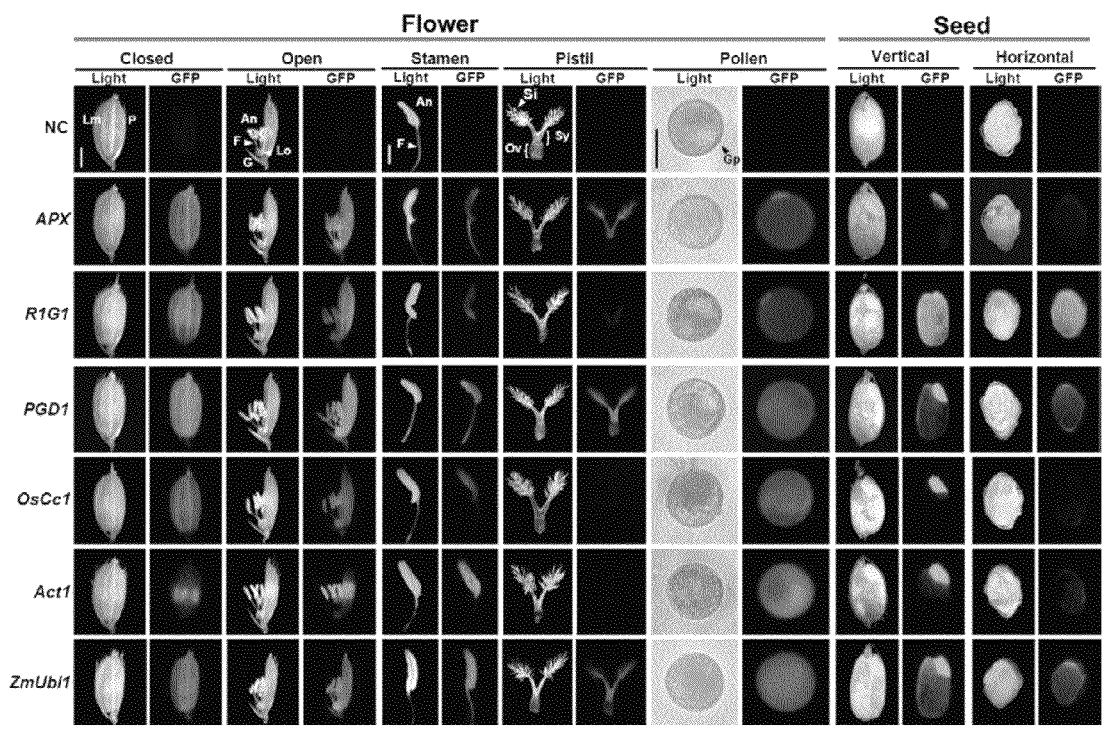
FIG. 10 shows the expression of GFP fluorescence in the flower and seed of transformed plant according to embodiments.

Observation of GFP Fluorescence in Reproductive Organ of Rice Transformed with Promoter GFP fluorescence was further examined in the flowers (spikelets) at the meiosis stage (FIG. 10). As found in the vegetative tissues, the transgenic flowers all showed a high level of GFP fluorescence. More specifically, the PGD1:gfp transgene directed high levels of GFP fluorescence in all of the floral organs including the lemma, palea, lodicule, glume, anther, filament, stigma, style, ovary and pollen, in a manner similar to ZmUbi1:gfp. GFP fluorescence in the APX:gfp flowers was also similar to that found for PGD1:gfp and ZmUbi1:gfp in all floral organs except for the ovary where no signal could be detected. In addition, zero or very low levels of GFP fluorescence were observed in a whole pistil and a filament of the stamen in the OsCc1:gfp, Act1:gfp and R1G1: gfp flowers. Hence, the APX and R1G1 promoters were found to be highly active in the whole plant body at both the vegetative and reproductive. Interestingly, the spatial activities of the PGD1 promoter were found to be strikingly similar to those of the ZmUbi1, a widely used constitutive promoter.

In the case of the APX promoter isolated in the present invention, GFP fluorescence was observed in the seed embryo in a manner similar to the case of OsCc1 and Act1. In the case of PGD1 and R1G1 promoters, GFP fluorescence was observed in all the embryo and endosperm in a manner similar to the case of ZmUbi. In the case of the R1G1 promoter, the uniform expression of GFP fluorescence was observed in the flower of the transformed rice. Particularly, in the case of the APX and PGD1 promoters, outstanding GFP fluorescence was observed in the flower anther and ovary.

As a result, in the case of the above-described constitutive expression promoters, (EP fluorescence was observed uniformly in all the tissues of the rice plants, including seeds and flowers.

The description of each gene shown in FIG. 10 is as follows: An: anther; F: filament; G: glume; Gp: germ pore; Lm: lemma; Lo: lodicule; Ov: ovary; P: palea; Si: stigma; Sy:

style; NC: negative control *Oryza sativa* L. cv Nakdong (non-transformed rice): ZmUbi: maize Ubi1 promoter; Act1: rice Actin1 promoter; and OsCc1: rice cytochrome c promoter.

Example 8

Levels of GFP Protein in the promoter:gfp Transgenic Rice Plants

Figure 11:
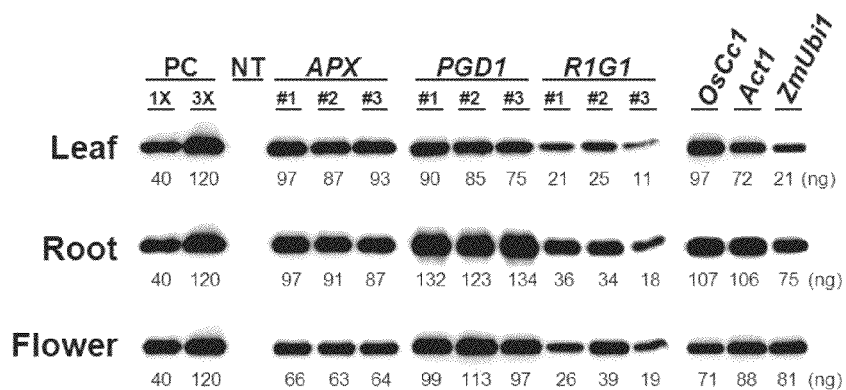
FIG. 11 shows levels of GFP protein in the promoter:gfp transgenic plants according to embodiments.

Protein extracts were prepared from the leaf and root tissues at 30 DAG and from flowers just before pollination. Three independent promoter:gfp transgenic plants and non-transgenic (NT) plants were analyzed. One line of each of the transgenic plants harboring the OsCc1, Act1 and ZmUbi1 gene promoters were included as constitutive controls. Ten μg of total soluble proteins were separated on a SDS-polyacrylamide gel, transferred to a membrane, and then immunoblotted with an anti-GFP antibody. The amount of GFP protein in promoter:gfp transgenic plants were calculated by comparing band intensities with those of known amounts of recombinant GFP protein used as positive controls (PC). The GFP protein levels of APX:gfp and PGD1:gfp plants were high and comparable to those of OsCc1:gfp, Act1:gfp and ZmUbi1:gfp plants (0.6 to 1.3% of the total soluble proteins; FIG. 11.). The GFP protein levels of R1G1:gfp plants ranged from 0.11 to 0.34% of the total soluble proteins depending on the specific transgenic lines and/or tissues.

What is claimed is:

1. A method comprising:
producing a target protein by transforming a plant using a vector comprising a promoter consisting of SEQ ID NO: 1 operably linked to a gene encoding said target protein.

2. The method of claim 1, wherein the target protein comprises at least one of interleukin, interferon, platelet-derived growth factor, hemoglobin, elastin, collagen, insulin, fibroblast growth factor, human growth factor, human serum albumin and erythropoietin.

3. A method comprising:
transforming a plant cell with a vector comprising a promoter consisting of SEQ ID NO: 1 operably linked to a gene coding sequence; and redifferentiating a transformed plant from the transformed plant cell.

* * * * *